(12) United States Patent
Surakitbanharn

(10) Patent No.: US 12,310,930 B2
(45) Date of Patent: *May 27, 2025

(54) STABILIZATION OF EPINEPHRINE FORMULATIONS

(71) Applicant: Yosyong Surakitbanharn, San Diego, CA (US)

(72) Inventor: Yosyong Surakitbanharn, San Diego, CA (US)

(73) Assignee: YS PHARMTECH, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,484

(22) Filed: Apr. 19, 2023

(65) Prior Publication Data

US 2023/0355551 A1 Nov. 9, 2023

Related U.S. Application Data

(63) Continuation of application No. 17/072,126, filed on Oct. 16, 2020, now abandoned, which is a continuation of application No. 16/310,728, filed as application No. PCT/US2017/037917 on Jun. 16, 2017, now abandoned.

(60) Provisional application No. 62/476,852, filed on Mar. 26, 2017, provisional application No. 62/351,462, filed on Jun. 17, 2016.

(51) Int. Cl.
*A61K 31/137* (2006.01)
*A61K 9/08* (2006.01)
*A61K 31/095* (2006.01)
*A61K 47/18* (2017.01)
*A61K 47/40* (2006.01)

(52) U.S. Cl.
CPC .............. *A61K 31/137* (2013.01); *A61K 9/08* (2013.01); *A61K 47/183* (2013.01); *A61K 47/40* (2013.01); *A61K 31/095* (2013.01)

(58) Field of Classification Search
None
See application file for complete search history.

(56) References Cited

U.S. PATENT DOCUMENTS 9,119,876 B1 9/2015 Kannan et al.
2007/0098748 A1 5/2007 Chen et al.
(Continued)

FOREIGN PATENT DOCUMENTS

WO 2014/127020 A1 8/2014

*Primary Examiner* — Bong-Sook Baek
(74) *Attorney, Agent, or Firm* — Stuart H. Mayer; Kaplan Breyer Schwarz LLP

(57) ABSTRACT

The disclosure herein relates to the innovative epinephrine formulations in aqueous solution of medicinal products that enhance the physicochemical stabilities of epinephrine and extend the product shelf life. In some instances, the formulations comprise epinephrine or a salt thereof, a complexing agent, and a "non-sulfite" antioxidant. The epinephrine formulations substantially demonstrated the superior physicochemical stabilities to conventional sulfite formulation of commercial medications currently available. In some instances, sulfite-free formulations further provide further benefit (e.g., safety benefits) to sulfite-sensitive patients. The compositions, methods for preparing the formulations, and methods of using the same (e.g., in the treatment of anaphylaxis) are also provided.

12 Claims, 9 Drawing Sheets

(56) References Cited

U.S. PATENT DOCUMENTS

| | | | |
|---|---|---|---|
| 2008/0269347 A1* | 10/2008 | Bruss | A61K 31/135 514/653 |
| 2015/0025154 A1 | 1/2015 | Miyano et al. | |
| 2015/0119440 A1 | 4/2015 | Karolchyk et al. | |
| 2015/0246009 A1 | 9/2015 | Gupta et al. | |
| 2015/0374832 A1 | 12/2015 | Surakitbanharn | |
| 2016/0058715 A1 | 3/2016 | Rakesh et al. | |

* cited by examiner

STABILIZATION OF EPINEPHRINE FORMULATIONS

CROSS-REFERENCE

This application is a continuation of U.S. application Ser. No. 16/310,728, filed Dec. 17, 2018, which is a National Stage of PCT/US2017/037917, filed Jun. 16, 2017 and claims the benefit of U.S. Provisional Application No. 62/351,462 filed on 17 Jun. 2016, and 62/476,852 filed on 26 Mar. 2017, both entitled "Stabilization of Epinephrine Formulations," and each of which are incorporated herein by reference in their entireties.

FIELD OF THE INVENTION

The invention generally relates to epinephrine formulations, particularly the physicochemical stability enhancement of epinephrine formulations (e.g., injection formulations (1:1000) in aqueous solution, such as for anaphylaxis treatment of anaphylactic shock).

BACKGROUND OF THE INVENTION

Epinephrine, more commonly known as adrenaline, is a hormone secreted by the medulla of the adrenal glands. Strong emotions such as fear or anger cause epinephrine to be released into the bloodstream, which causes an increase in heart rate, muscle strength, blood pressure, and sugar metabolism. This reaction, known as the "Flight or Fight Response", prepares the body for strenuous activity. Epinephrine is found in small amounts in the body and is essential for maintaining cardiovascular homeostasis because of its ability to divert blood to tissues under stress.

In medicine, epinephrine is used mainly as a stimulant in cardiac arrest, as a vasoconstrictor in shock, and as a bronchodilator and antispasmodic in bronchial asthma. Its uses also include, e.g., combating low blood pressure during hemorrhagic, allergic or anaphylactic shock; opening the airways during thematic attack; restricting the distribution of locally administered drugs such as local anesthetics; reducing nasal congestion; reducing the amount of fluid in the eye to decrease intraocular pressure and/or as a performance aid in emergency situations.

Allergic emergencies, such as anaphylaxis, are a growing concern, given the increasing awareness of members of the public of their frequency and potential severity. Anaphylaxis is a sudden, severe, systemic allergic reaction that can be fatal, in many cases, if left untreated. Anaphylaxis can involve various areas of the body, such as the skin, respiratory tract, gastrointestinal tract, and cardiovascular system. Acute symptoms occur from within minutes to two hours after contact with the allergy-causing substance, but in rare instances onset may be delayed by as much as four hours. Contact with anaphylaxis-inducing agents, and the severity of the resulting anaphylactic reaction, can be extremely unpredictable. Accordingly, allergists recommend that persons who have a personal or family history of anaphylaxis be prepared to self-administer emergency treatment at all times. Additionally, adults charged with caring for children who are at risk for anaphylaxis should also be prepared to administer anti-anaphylactic first aid.

The symptoms of anaphylaxis include one or more of the following, generally within 1 to about 15 minutes of exposure to the antigen: agitation, a feeling of uneasiness, flushing, palpitations, paresthesias, pruritus, throbbing in the ears, coughing, sneezing, urticaria, angioedema, difficulty breathing due to laryngeal edema or bronchospasm, nausea, vomiting, abdominal pain, diarrhea, shock, convulsions, incontinence, unresponsiveness and death. An anaphylactic reaction may include cardiovascular collapse, even in the absence of respiratory symptoms.

Due to its vasoconstrictive effects, epinephrine is the drug of choice for treating anaphylaxis. Allergy patients undergoing immunotherapy may receive an adrenaline rinse before the allergen extract is administered, thus reducing the immune response to the administered allergen.

Epinephrine in aqueous solution deteriorates rapidly on exposure to air or light or heat and discolors to pink from the oxidation to adrenochrome and to brown from the formation of melanin.

Epinephrine is a catechol compound that is sensitive to oxidation to o-quinones, which can react further to form highly colored compounds. Epinephrine can thus react to form adrenochrome, a highly colored indole derivative. The rate of this reaction increases with pH, temperature and by the presence of metal ions, such as aluminum from various rubbers and iron from amber glassware. Epinephrine solutions may also lose potency as a result of racemization, and protection from light minimizes this form of instability.

The modification or degradation of the catechol amines is undesirable for a number of reasons. Modification of the catechol amine results in loss of titer of the active ingredient, formation of compounds which may have undesirable physiological effects, and the appearance of a dark color, which makes the solution offensive and unmarketable. The initial loss of active compound due to auto-oxidation during the preparation and packaging of such a solution is substantial despite the fact that such procedures are carried out as nearly as practically possible in an inert atmosphere. Such a solution must be stored under refrigeration in order to decrease the rate of deterioration of the compound and thus prolong its shelf-life.

It is a standard practice, in order to stabilize adrenergic compounds such as catechol amines against auto-oxidation, to combine the same with an antioxidant. Various antioxidants which have been used to stabilize catechol amine solution in a variety of formulations such as aerosols, eye-drops, injections etc. including metabisulfite, bisulfite, sulfite, ascorbic acid, thioglycollate, thioglycerol, cysteine, propyl gallate and formaldehyde sulfoxylate (References: GB 425678, GB 930452, U.S. Pat. Nos. 3,149,035, 3,966, 905, CA 981182, US 2008/0269347 A1, DD-A1-150 694, WO 94/13274, WO 97/16196, WO98/20869, U.S. Pat. No. 4,734,438).

For anaphylactic treatment, the usual epinephrine concentration is 0.3-0.5 mg in 1:1000 dilution for subcutaneous or intramuscular injection, which is commercially available in auto injector devices such as EpiPen®, Twinject®, Adrenaclick® and Auvi-Q™. For instance according to its prescribing information, EpiPen® is designed to deliver a minimum of 0.3 mg epinephrine in a 0.3 mL injection volume. Its composition in 1 mL water for injection consists of either 1.0 mg epinephrine as free base, 6.0 mg sodium chloride, 1.7 mg sodium metabisulfite and hydrochloric acid to adjust pH 2.2-5.0. Twinject® and Adrenaclick® has a comparable composition to Epipen®, but instead uses sodium bisulfite as an antioxidant and includes chlorobutanol as a preservative. Auvi-Q™ has a comparable composition to Twinject® and Adrenaclick® in an absence of chlorobutanol.

Note that a sulfite related compound i.e. sodium metabisulfite or sodium bisulfite, which is commonly used in the conventional epinephrine formulations as an antioxidant, has been associated with some other severe allergic reactions (EpiPen® Prescribing Information 2014; Auvi-Q™ Prescribing Information 2014; Adrenaclick® Prescribing Information 2013; The Australasian Society of Clinical Immunology and Allergy (ASCIA), *Sulfite Sensitivity*, 2014; Papaioannou R. and Pfeiffer C. C., *Sulfite Sensitivity*, Journal of Orthomolecular Psychiatry, 13(2), 105-110, 1984). In addition, sodium bisulfite can directly react with epinephrine to rapidly reduce its potency and produce a degradation product, epinephrine sulfonic acid (ESA). The increase of ESA in the epinephrine formulation containing a sulfite related compound could be greater than 15% at the end of product life (about 12-18 months). The safety and/or toxicity of ESA in commercial epinephrine products for anaphylactic treatment are still not well understood. In addition, the potency of epinephrine also could be substantially degraded due to such reaction to nearly 20% at the end of product life.

Therefore all commercial products on the market must overage about 10-12% epinephrine during the manufacturing process in order to compensate a fast decay of its potency. This means that any patient who received epinephrine injection at the beginning versus the end of product life might have 20% dose variation during an emergency treatment. The actual shelf lives of all commercial products would be shortened if they are exposed to a higher temperature than a room temperature i.e. 25° C. for a period of time. In addition, all commercial products must have clear windows on the injection devices e.g. auto injectors to observe the product discolorations and warnings of the product exposures to excursion temperatures on the labels.

Thermally induced epinephrine degradation in an aqueous solution is not only the oxidation process but also the racemization one as well. An active drug isomer, l-epinephrine can be rearranged to produce a little or no pharmacological isomer of d-epinephrine. The epinephrine racemization in commercial formulations was reported to be ~10% d-isomer after ~4 year storage at pH 2.4 or after ~3 year at pH 3.0-3.5 (Stepensky D., Chorny M., Dabour Z. and Schumacher I., *Long-Term Stability Study of L-Adrenaline Injections: Kinetics of Sulfonation and Racemization Pathways of Drug Degradation*; Journal of Pharmaceutical Sciences., 93(4), 969-980, 2004). A commercially approved product, Adrenalin® 1 mL and 30 mL have a limitation of ≤9.5% d-epinephrine content at the end of shelf lives for 18 and 14 months, respectively (U.S. Pat. No. 9,119,876 B1).

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY OF THE INVENTION

Provided in certain embodiments herein are epinephrine compositions (e.g., aqueous formulations), such as that have good physicochemical stability. In some instances, the compositions provided herein provide excellent physicochemical stability, while using very small amounts of antioxidants, complexing agents, and/or other additives. In certain instances, compositions provided herein surprisingly demonstrate greatly improved physicochemical stability by greatly reducing the amounts of additives included. In specific embodiments, compositions provided herein have good potency retention, good visual characteristics (i.e., colorlessness), and low formation of degradation products, even at rigorous storage conditions.

Also provided herein are compositions and methods for the treatment of anaphylaxis (or any of the symptoms associated therewith, such as described herein), anaphylactic shock, or the like. In another embodiment, provided herein are compositions and methods for treating cardiac arrest, bronchial asthma, croup, nasal congestion, reducing fluid in the eye, decreasing intraocular pressure, and/or treating glaucoma.

In specific embodiments, compositions provided herein are aqueous formulations. In some instances, also provided herein are methods for enhancing the physicochemical stability of epinephrine in aqueous solution, such as by formulating epinephrine in accordance with the disclosures herein. In specific embodiments, formulation of compositions herein comprises utilization of epinephrine with a complexing agent, such as a native or modified cyclodextrin derivative to provide an inclusion complex with epinephrine ((−)-3,4-Dihydroxy-α-[(methylamino)methyl]benzyl alcohol). In further or alternative embodiments, formulation of compositions herein comprises utilization of epinephrine with an antioxidant, such as cysteine, or a combination of antioxidants. Surprisingly, it is found and illustrated in certain embodiments herein that very low relative amounts of antioxidant are preferred in order to provide good physicochemical stability. Formulation of such compositions optionally comprises additional agents, such as described herein in the amounts described herein. In certain embodiments, epinephrine and other agents included in the composition are combined into the formulation in either neutral (e.g., free base or acid) or salt form, such as discussed in more detail herein. In a specific embodiment, provided herein is a method of preparing a pharmaceutical composition (e.g., aqueous solution) comprising combining epinephrine or a pharmaceutically acceptable salt thereof, with one or more antioxidant (such as described herein) or a pharmaceutically acceptable salt thereof, a pH buffering agent or a pharmaceutically acceptable salt thereof, a chelating agent or a pharmaceutically acceptable salt thereof, and a tonicity modifier into an aqueous medium. In more specific embodiments, the process further comprises combining a complexing agent or a pharmaceutically acceptable salt thereof therewith. In certain instances, compositions described herein as comprising an agent optionally comprise the agent as described, an ion (e.g., pharmaceutically acceptable ion) thereof, a salt (e.g., pharmaceutically acceptable salt) thereof, or a solvate (e.g., hydrate) thereof, or the like, as applicable.

In certain embodiments, provided herein is epinephrine and one or more antioxidant. In some instances, at very low concentrations of antioxidant, rapid degradation of epinephrine is observed. In additional instances, at higher concentrations of antioxidant, undesirable degradation of epinephrine occurs over time. In certain embodiments herein, antioxidant is provided in an amount to provide good stability of epinephrine initially, and over time, such as described in more detail herein. In some embodiments, the antioxidant is cysteine, acetylcysteine, thioglycerol, or any combination thereof. In various embodiments, other antioxidants, such as described herein are used in addition to and/or instead of such antioxidants. In certain embodiments, antioxidants are provided in the composition in a (e.g., combined or total) amount as described herein, such as about 0.005 wt. % to less than 0.1 wt. %. In specific embodiments, antioxidant is present in an amount of about 0.005 wt. % to about 0.07 wt. %. In more specific embodiments, antioxidant is present in an amount of about 0.005 wt. % to about 0.05 wt. %. In still more specific embodiments, antioxidant is present in an amount of about 0.005 wt. % to about 0.035 wt. %. In yet more specific embodiments, antioxidant is present in an amount of about 0.005 wt. % to about 0.03 wt. %. In some embodiments, antioxidant is present in an amount of about 0.01 wt. % to less than 0.1 wt. %. In specific embodiments, antioxidant is present in an amount of about 0.01 wt. % to about 0.07 wt. %. In specific embodiments, antioxidant is present in an amount of about 0.01 wt. % to about 0.07 wt. %. In more specific embodiments, antioxidant is present in an amount of about 0.01 wt. % to about 0.05 wt. %. In still more specific embodiments, antioxidant is present in an amount of about 0.01 wt. % to about 0.035 wt. %. In yet more specific embodiments, antioxidant is present in an amount of about 0.01 wt. % to about 0.03 wt. %. In further embodiments, the composition further comprises antioxidant, a pH buffering agent, a chelating agent, and a tonicity modifier. In yet further embodiments, a composition provided herein further comprises a complexing agent (e.g., cyclodextrin).

In one embodiment, a composition provided herein comprises epinephrine, complexing agent, antioxidant, pH buffering agent, chelating agent and tonicity modifier in an aqueous based media. In some embodiments, a provided herein comprises epinephrine, antioxidant, pH buffering agent, chelating agent and tonicity modifier in an aqueous based media.

In specific embodiments, provided herein is a pharmaceutical composition comprising:
  a. epinephrine;
  b. complexing agent (e.g., a cyclodextrin) (e.g., in a molar ratio of complexing agent-to-epinephrine of about 1:10 to about 10:1);
  c. antioxidant (e.g., cysteine) (e.g., in an amount of less than 0.1 wt. %, about 0.01 wt % to about 0.07 wt. %, about 0.01 wt. % to about 0.05 wt. %, or the like);
  d. pH buffering agent;
  e. chelating agent;
  f. tonicity modifier; and
  g. an aqueous medium.

In certain embodiments, a composition provided herein has good physicochemical stability. In some embodiments, after six months of storage at 40° C. and 75% relative humidity (RH), the composition comprises at least 90 wt. % (e.g., at least 95 wt. %) of the epinephrine in the composition prior to storage. In further or alternative embodiments, after six months of storage at 40° C. and 75% relative humidity (RH), the composition comprises less than 10 wt. % (e.g., less than 5 wt. %) epinephrine degradant. In certain embodiments, a composition provided herein has a shelf life (e.g., retaining at least 90 wt. % (e.g., at least 95 wt. %) initial epinephrine) (e.g., at conditions of about 25° C., such as at 60% RH) of at least 2 years, such as at least 2.5 years, or at least 3 years. In some embodiments, after storage (e.g., after 3.5 months or six months of storage at 40° C. and 75% relative humidity (RH)), less than 10 wt. % of the epinephrine in a composition provided herein is d-epinephrine. In specific embodiments, less than 9.5 wt. %, less than 6 wt. %, less than 5 wt. %, or less than 3 wt. % of the epinephrine in a composition provided herein is d-epinephrine after storage (e.g., after storage for at least 1 year, 2 years, or 3 years at conditions of about 25° C., such as at 60% RH, or for at least 3.5 months or 6 months at 40° C. and 75% RH). In certain instances, such temperatures are generally kept within ±2° C. and such relative humidities are generally kept within ±5%. In certain embodiments, a composition provided herein after 12 months of storage at 25±2° C. and 60±5% relative humidity (RH), (i) the composition comprises at least 90 wt. % (e.g., at least 95 wt. %, at least 97 wt. %, at least 98 wt. %, or the like) of the epinephrine in the composition prior to storage; and/or (ii) the composition is substantially colorless In addition to retaining good potency over extended periods of time, compositions provided in certain embodiments herein also possess good visual characteristics and minimal formation of degradation products as well. In some embodiments, the compositions provided herein substantially retain their colorless nature, even after long and/or rigorous storage conditions. In specific embodiments, the compositions provided herein remain substantially colorless (e.g., colorless to the naked eye) after storage for at least 2 years, at least 3 years or the like (such as at about 25° C., e.g., at 60% RH). In further or alternative embodiments, compositions provided herein remain substantially colorless (e.g., colorless to the naked eye) after (e.g., six months) of storage at 40° C./75% RH. In certain embodiments, after storage for at least 2 years, at least 3 years or the like (such as at about 25° C., e.g., at 60% RH) a composition provided herein (e.g., comprising about 0.1 wt. % epinephrine) has an optical density (O.D.) (e.g., absorbance at a maximum wavelength or λmax at 485 nm) of less than 0.1, e.g., less than 0.05, less than 0.02, less than 0.01, or the like. In further or alternative embodiments, after storage for at least 6 months (such as at about 40° C., e.g., at 75% RH) a composition provided herein (e.g., comprising about 0.1 wt. % epinephrine) has an optical density (O.D.) (absorbance at a maximum wavelength or λmax at 485 nm) of less than 0.1, e.g., less than 0.05, less than 0.02, less than 0.01, or the like.

In certain embodiments, compositions provided herein comprise epinephrine in an amount suitable for therapeutic benefit. In specific embodiments, the composition comprises about 0.0001 wt. % to about 1 wt. % (e.g., about 0.001 wt. % to about 1 wt. %, or about 0.01 wt. % to about 1 wt. %), or more, epinephrine. In more specific embodiments, such as in (1:1000) formulations (e.g., which are optionally utilized in the treatment of anaphylactic shock, anaphylaxis, or the like), compositions provided herein comprise about 0.05 wt. % to about 0.15 wt. %, such as about 0.1 wt. % epinephrine. In specific embodiments, a composition provided herein comprises about 0.05 wt. % or about 0.5 mg/mL of epinephrine (e.g., on a free base weight basis), such as a formulation (1:2000) for certain pediatric uses. In other specific embodiments, a composition provided herein comprises about 0.1 wt. % or about 1 mg/mL of epinephrine (e.g., on a free base weight basis), such as a formulation (1:1000) for certain adult uses. In some embodiments, epinephrine is formulated into a composition herein as a free base or as a pharmaceutically acceptable salt thereof, such as described herein.

In certain embodiments, a composition provided herein comprises a cyclodextrin (e.g., as a complexing agent thereof). In specific embodiments, the cyclodextrin is sulfobutylether ß-cyclodextrin (SBEßCD) or hydroxypropyl ß-cyclodextrin (HPßCD). In some embodiments, the cyclodextrin is present in the composition in a cyclodextrin-to-epinephrine molar ratio of about 1:10 to about 10:1, e.g., about 1:3 to about 2:1 (e.g., about 1:2.5 to about 1:1.5). In further or alternative embodiments, the composition comprises about 0.001 wt. % to about 10 wt. % (e.g., about 0.01 wt. % to about 10 wt. %) complexing agent. In other embodiments, a complexing agent, such as cyclodextrin, is omitted from the formulation.

In some embodiments, a composition provided herein comprises a cysteine (e.g., as an antioxidant thereof). In certain embodiments, the cysteine is present in the composition in a weight ratio of cysteine-to-epinephrine of about 1:2 or less, or about 1:5 or less (e.g., down to about 1:50, or about 1:20). In specific embodiments, the cysteine is present in the composition in a weight ratio of cysteine-to-epinephrine of about 1:10. In further or alternative embodiments, the composition comprises to be less than 0.05 wt. % cysteine, such as about 0.03 wt. % or less, or about 0.02 wt. % or less. In certain embodiments, the composition comprises about 0.001 wt. % cysteine or more (e.g., about 0.001 wt. % to about 0.05 wt. %), such as about 0.005 wt. % or more (e.g., 0.005 wt. % to about 0.05 wt. %).

In certain embodiments, a composition provided herein comprises citrate and/or citric acid (e.g., as a buffering agent thereof) (e.g., the relative concentration and presence of citrate and/or citric acid present in an aqueous composition depending on the pH of thereof). In certain embodiments, the composition comprises about 0.01 wt. % or less of citric acid and citrate combined (e.g., about 0.001 wt. % to about 0.01 wt.

In some embodiments, the pH of a composition provided herein is about 2 to about 5 (e.g., about 2 to about 4). In specific embodiments, the pH of the composition is about 2.5 to about 3.5.

In certain embodiments, a composition provided herein comprises edetate (e.g., as a chelating agent). In some embodiments, the composition comprises about 0.01 wt. % of edetate or less (e.g., about 0.001 wt. % to about 0.01 wt. %).

In some embodiments, a composition provided herein has an osmolality in the range of about 200 mOsm/kg to about 400 mOsm/kg. In certain embodiments, a tonicity modifier is present in the composition in an amount suitable to provide a solution osmolality in the range of about 200 mOsm/kg to about 400 mOsm/kg. In some embodiments, a composition provided herein is formulated with a salt, such as sodium chloride, as a tonicity modifier, which would be dissolved at least partially dissolved in an aqueous medium. In some embodiments, a composition provided herein comprises about 0.01 wt. % to about 5 wt. % (e.g., about 0.1 wt. % to about 1 wt. %) of a tonicity modifier (e.g., dissolved sodium chloride).

In specific embodiments, provided herein is a pharmaceutical composition comprising:
a. epinephrine;
b. complexing agent (e.g., cyclodextrin) (e.g., in a molar ratio of complexing agent-to-epinephrine of about 1:10 to about 10:1);
c. antioxidant (e.g., cysteine, acetylcysteine, thioglycerol, or any combination thereof) (e.g., in a (combined) amount of less than 0.1 wt. %, such as about 0.07 wt. % or less, about 0.05 wt. % or less, about 0.035 wt. % or less, or about 0.03 wt. % or less, e.g., down to about 0.01 wt. % or down to about 0.005 wt. %);
d. a pH buffering agent;
e. a chelating agent;
f. a tonicity modifier; and
g. an aqueous medium.

In some embodiments, provided herein is a pharmaceutical composition comprising:
a. epinephrine;
b. antioxidant (e.g., cysteine, acetylcysteine, thioglycerol, or any combination thereof) (e.g., in a (combined) amount of less than 0.1 wt. %, such as about 0.07 wt. % or less, about 0.05 wt. % or less, about 0.035 wt. % or less, or about 0.03 wt. % or less, e.g., down to about 0.01 wt. % or down to about 0.005 wt. %);
c. pH buffering agent;
d. chelating agent;
e. tonicity modifier; and
f. an aqueous medium.

In specific embodiments, provided herein is a pharmaceutical composition comprising:
a. epinephrine;
b. cysteine (e.g., in an amount of less than 0.1 wt. %, such as about 0.07 wt. % or less, about 0.05 wt. % or less, about 0.035 wt. % or less, or about 0.03 wt. % or less, e.g., down to about 0.01 wt. % or down to about 0.005 wt. %);
c. a pH buffering agent;
d. a chelating agent;
e. a tonicity modifier; and
f. an aqueous medium.

In various embodiments, specific details of any of such compositions are such as described above and herein.

In specific embodiments, pharmaceutical compositions provided herein are formulated for injection. In such embodiments, the aqueous medium utilized is water suitable for injection (WFI). In specific embodiments, such water is sterile. In some embodiments, the composition is loaded into an administrative device, such as a device for administering the composition to an individual via injection. In specific embodiments, the administrative device is a syringe or a cartridge suitable for use in a manual and/or auto injector (e.g., that can precisely and accurately deliver effective amount of epinephrine medication).

Provided in various embodiments herein are compositions comprising (or formulated with) epinephrine (e.g., formulated as a free base) as an active pharmaceutical ingredient and used at a range of about 0.0001-1.0% (e.g., based on free base concentration). In some embodiments, the composition comprises a modified ß-cyclodextrin, such as either hydroxypropyl β-cyclodextrin (HPßCD) or sulfobutyl ether β-cyclodextrin (SBEßCD) (e.g., as a complexing agent), in a molar ratio of cyclodextrin-to-epinephrine of about 1:10 to about 10:1 (e.g., about 1:3 to about 2:1). Within further or additional embodiments, the composition comprises (or is formulated with) cysteine (L-cysteine) (e.g., as an antioxidant) at a concentration of about 0.005 wt. % to 0.1 wt. %, (e.g., about 0.005 wt. % to about 0.07 wt. %, about 0.005 wt. % to about 0.05 wt. %, about 0.005 wt. % to about 0.035 wt. %, about 0.005 wt. % to about 0.03 wt. %, or the like, such as above 0.01 wt. %) or a weight ratio of cysteine-to-epinephrine of about 1:20 to about 1:2 (e.g., about 1:20 to about 1:5, about 1:20 to about 1:10, or about 1:10). Within certain embodiments, the composition comprises (or is formulated with) citric acid/citrate as a pH buffering agent at a concentration of about 0.005 wt. % to about 0.05 wt. % or at a weight ratio of citric acid-to-epinephrine of about 1:20 to about 1:2 (e.g., about 1:20 to about 1:5, about 1:20 to about 1:10, or about 1:10). In further or alternative embodiments, compositions provided herein comprise (or is formulated with) edetate (e.g., formulated as edetate disodium) (e.g., as a chelating agent) at a concentration of about 0.005 wt. % to about 0.05 wt. % or a weight ratio of edetate-to-drug of about 1:20 to about 1:2 (e.g., about 1:20 to about 1:5, about 1:20 to about 1:10, or about 1:10).

In certain embodiments, provided herein is a method of treating anaphylactic shock, anaphylaxis, or other allergic reaction by administering a composition provided herein to an individual in need thereof. In specific embodiments, a composition provided herein is administered by intramuscular injection or subcutaneous injection or intravenous injection, such as with a syringe or a manual and/or auto injector (such as described herein).

In some embodiments, provided herein are methods of preparing (e.g., physiochemically stable) pharmaceutical compositions comprising epinephrine (e.g., for treating anaphylaxis or anaphylaxis shock, such as by injection), the methods comprising combining in an aqueous medium:
  a. epinephrine, or a pharmaceutically acceptable salt thereof;
  b. cysteine (e.g., in an amount of less than 0.05 wt. %), or a pharmaceutically acceptable salt thereof;
  c. a pH buffering agent (e.g., citric acid, or other agent, such as described herein);
  d. a chelating agent (e.g., edetate or a pharmaceutically acceptable salt thereof); and
  e. a tonicity modifier (e.g., sodium chloride or dextrose).

In specific embodiments, the agents are optionally combined into a single aqueous medium, or combined in parts of the aqueous medium prior to combing the parts of the aqueous medium to formulate the final composition. In one specific embodiment, the epinephrine is combined into a first aqueous medium part, the remainder cysteine, pH buffering agent and chelating agent are combined into a second aqueous medium part, before the first and second aqueous medium parts are combined. In some embodiments, a tonicity modifier is added to achieve the desired osmolality to the first part, the second part, and/or the combination thereof. In addition, in some embodiments, the method further comprises combining a complexing agent (e.g., in a molar ratio (complexing agent-to-epinephrine) of about 10:1 to about 1:10, such as described herein) into the composition, the complexing agent optionally being added at any point, such as to the first part, the second part, or the combination thereof. Other variants are also contemplated by the methods herein, such as wherein each component is individually dissolved in its own aqueous medium part prior to combination. In addition, in some instances, the combined parts are optionally further diluted (e.g., with an aqueous medium having the osmolality in the range of that desired for the final product, such as about 200 mOsm/kg to about 400 mOsm/kg) to achieve the desired volume and concentration. Exemplary concentrations and specific types of agents utilized in such methods are as described herein.

In certain embodiments, provided herein is an aqueous composition comprising epinephrine (e.g., as a free base, ion, solvate, salt, etc. thereof) in a concentration (e.g., based on the concentration of the free base) of about 0.001 mg/mL to about 50 mg/mL, or, e.g., about 0.5 mg/mL to about 1.5 mg/mL, or about 1 mg/mL. In some embodiments, provided herein is an aqueous composition comprising a complexing agent (e.g., a cyclodextrin, such as SBEßCD described herein) in a concentration of about 1.2 mg/mL to about 24 mg/mL, such as about 5 mg/mL to about 7 mg/mL or about 6 mg/mL. In some embodiments, provided herein is an aqueous composition comprising a complexing agent (e.g., a cyclodextrin, such as HPßCD described herein) in a concentration of about 0.8 mg/mL to about 16 mg/mL, such as about 3 mg/mL to about 5 mg/mL or about 4 mg/mL. In some embodiments, provided herein is an aqueous composition comprising an antioxidant (e.g., cysteine (e.g., as a free base, ion, solvate, salt, etc. thereof)) in a concentration of about 0.5 mg/mL or less, such as about 0.2 mg/mL or less, about 0.001 to about 0.5 mg/mL, about 0.01 mg/mL to about 0.2 mg/mL, about 0.05 to about 0.15 mg/mL, or about 0.1 mg/mL. In certain embodiments, provided herein is an aqueous composition comprising a buffering agent (e.g., citric acid/citrate (e.g., comprising both free acid and conjugate base forms)) in a concentration of about 5 mg/mL or less, such as about 1 mg/mL or less, about 0.5 mg/mL or less, about 0.2 mg/mL or less, about 0.001 to about 0.5 mg/mL, about 0.01 mg/mL to about 0.2 mg/mL, about 0.05 to about 0.15 mg/mL, or about 0.1 mg/mL. In certain embodiments, provided herein is an aqueous composition comprising a chelating agent (e.g., edetate, such as in a form described herein) in a concentration of about 5 mg/mL or less, such as about 1 mg/mL or less, about 0.5 mg/mL or less, about 0.2 mg/mL or less, about 0.001 to about 0.5 mg/mL, about 0.01 mg/mL to about 0.2 mg/mL, about 0.05 to about 0.15 mg/mL, or about 0.1 mg/mL. In certain embodiments, pharmaceutical compositions are prepared utilizing agents in such amounts. In certain embodiments, while in some instances formulation provided herein are prepared using a salt (e.g., pharmaceutically acceptable salt) of an agent herein (epinephrine), weight percentages are provided using the weight percentage of the free base of the agent provided, rather than the salt utilized to formulate the composition.

This "Summary of the Invention" or "Summary" section is provided to introduce a selection of concepts in a simplified form. The concepts are further described in the "Detailed Description of the Invention" section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

In specific embodiments, compositions and formulations provided herein are sulfite free, or do not comprise sulfite, such as metabisulfite and/or bisulfite. In certain embodiments, the amount of sulfite in a composition provided herein is less than 0.001 wt. % (e.g., less than 0.0001 wt. %).

In some embodiments, compositions described herein are formulated for parenteral administration (e.g., intramuscular injection or subcutaneous injection or intravenous injection), topical administration, spray administration (e.g., nasal administration, buccal, or sublingual administration), pulmonary administration (e.g., by inhalation following aerosolization or nebulization), ophthalmic administration, oral administration, or the like. In certain embodiments, provided herein are compositions suitable for administration via such techniques. In some embodiments, such compositions comprise epinephrine (or a pharmaceutically acceptable salt, ion, solvate, or the like thereof) and other optional components (e.g., a complexing agent, such as a cyclodextrin, and/or antioxidant, such as a cysteine), such as in the ratios and/or weights described herein.

In a specific embodiment, a composition herein formulated into pharmaceutical dosage forms of a solid or gel dosage form, such as a fast dissolving composition, e.g., an orally disintegrating or dissolving tablet or other dosage form. In specific embodiments, a solid dosage form optionally comprises a lyophilized formulation (e.g., lyophilized from an aqueous formulation, such as described herein). In certain embodiments, such compositions are administered and/or suitable for buccal and/or sublingual administration via mucosal tissue absorption in the mouth. In another specific embodiment, a composition provided herein is formulated into pharmaceutical dosage forms suitable for parenteral medication by (re)constituting a lyophilized formulation, such as described herein, into a solution. In certain embodiments, such (re)constituted compositions are then administered by suitable methods, such as via intramuscular injection, subcutaneous injection, or intravenous injection. In some embodiments, a composition provided herein is formulated as a topical medication, such as a solution, patch, cream, ointment, gel or the like. In specific embodiments, such formulations are suitable for topical administration to (and absorption by) the skin (e.g., intact or broken skin). In some embodiments, a composition herein is formulated as a spray medication, such as for administration via nasal absorption, buccal and/or sublingual absorptions, and/or topical absorption via the skin (e.g., broken or intact). In certain embodiments, the composition is formulated as an inhalation medication. In specific embodiments, such formulations are administered by nebulization into aerosol and administrating drug via pulmonary absorption. In some embodiments, a composition herein is formulated as an ophthalmic medication. In specific embodiments, such formulations are in the form of a solution, cream, ointment, gel or the like. In some embodiments, such compositions or formulations are administered for intraocular absorption.

Compositions and formulations described herein are administered by and using any suitable method and/or device. In specific embodiments, a composition or formulation provided herein is loaded into an administrative device that delivers an effective amount of medication. In specific embodiments, the administrative device is, by way of non-limiting example, a syringe or a cartridge suitable for delivering parenteral medications via a manual and/or auto injector, a syringe or an actuator suitable for delivering a spray medication, a nebulizer suitable for delivering an aerosol medication, and an applicator or dropper or container (e.g. bottle or squeezable tube) suitable for delivering ophthalmic and topical medications.

In some embodiments, provided herein are methods of restricting the distribution of locally administered drugs such as local anesthetics for parenteral administration or topical administration (e.g., for both intact and broken skins), such as by using a composition herein formulating with an anesthetic agent or anesthetic agents. In some embodiments, provided herein is a method of providing anesthesia to an individual by administering a composition described herein and further comprising an anesthetic agent or anesthetic agents (e.g., articaine, bupivacaine, chloroprocaine, cocaine, etidocaine, lidocaine, mepivacaine, prilocaine, procaine, ropivacaine, tetracaine and/or a combination thereof).

In some embodiments, concentrations are described herein. In specific instances, the concentration refers to the concentration of a compound itself or the free base thereof, with explicit disclosure for both being contemplated in each instance. For example, a disclosure referring to the concentration of an epinephrine salt herein refers to express disclosure of the concentration of the salt itself and the concentration of epinephrine (free base), unless otherwise noted.

In certain disclosures herein, a composition comprising an agent is described. Generally, the disclosure includes disclosure of and reference to the agent itself, salts thereof (e.g., pharmaceutically acceptable salts thereof), solvates thereof (e.g., hydrates), ions thereof, a free base thereof, conjugate acid thereof, and the like. For example, disclosure and claims of a composition herein comprising epinephrine herein includes disclosure of and reference to compositions comprising epinephrine, salts thereof, free base thereof, ions thereof, solvates thereof, and the like, unless otherwise noted.

In various embodiments herein, compositions and methods provided herein describe the use of "a" or "an" agent. Such disclosures include disclosure of and reference to "one and only one" and "one or more" of such agent(s), unless otherwise noted. In some instances, wherein multiple agents are utilized, reference to concentrations of "a" or "an" such agent includes reference to the combined concentration of the multiple agents.

In certain embodiments, disclosure of a value herein includes disclosure of a value about equal to that value. In various embodiments, a value is "about" the value if it is between ½ and 2× that value, such as about ±50%, ±20%, ±10%, ±5%, or the like. In addition, any disclosure of a value "about" a specific number includes disclosure of that number itself. For example, disclosure of a range of about 0.01 wt. % to about 0.07 wt. % of epinephrine herein includes disclosure of 0.01 wt. % to 0.07 wt. %.

DETAILED DESCRIPTION OF THE INVENTION

Figure 1:
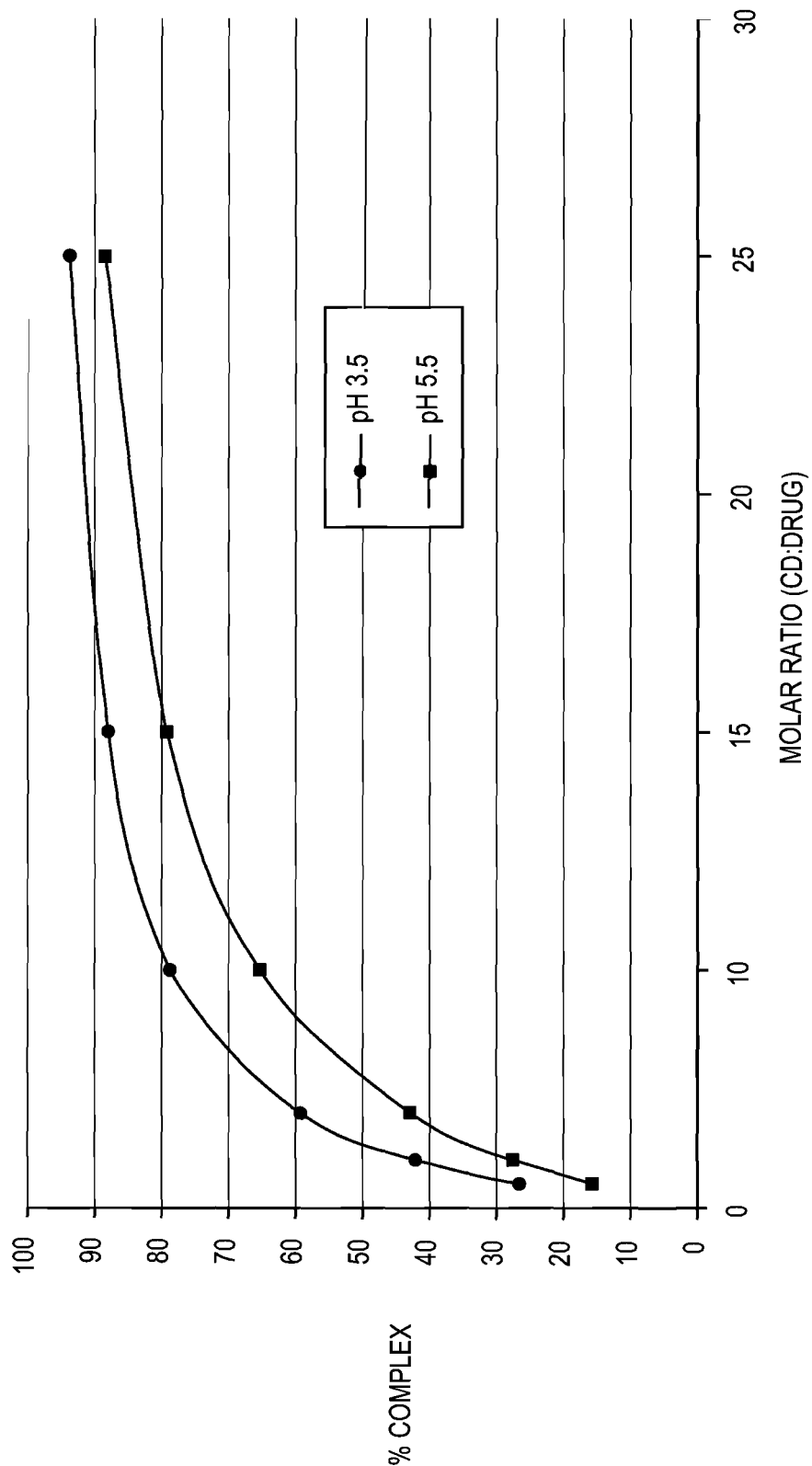
FIG. 1 demonstrated the fraction of epinephrine complex with SBEßCD at pH 3.5 (K=488 M$^{-1}$) and pH 5.5 (K=111 M$^{-1}$).

In order to prevent the thermal and/or oxidative degradations of epinephrine, commercial formulations available on the market are currently using a common conventional antioxidant of sulfite related compounds such as sodium bisulfite and/or sodium metabisulfite etc. The examples of marketed products of epinephrine auto injectors for anaphylaxis treatment include EpiPen®, Twinject®, Adenaclick® and Auvi-Q™. The sulfite related compounds can directly react with epinephrine, resulting in a substantial loss of epinephrine potency and generating degradation products, such as epinephrine sulfonic acid (ESA), which rapidly increases with time and becomes a major limiting factor to the product shelf life.

In some instances, sulfite related compounds in foods and/or medications cause a severe allergy or asthma reaction. For instance, some people have experienced severe reactions from sulfite-containing medications including intravenous drugs and inhaled medications, these reactions including flushing, hives, and a drop in lung function. The present invention provides the compositions of a "sulfite free" formulation of epinephrine, which significantly improves the product stability and eliminates the patient's risk of a potential exposure to a severe allergy or asthma reaction from the aforementioned antioxidant of sulfite related compounds.

In certain embodiments, present invention provides compositions and methods of using a novel formulation to enhance the physicochemical stability of epinephrine in an aqueous solution and subsequently extend the product shelf life. In some embodiments, the invention also provides a safer medication for patients by reducing and/or eliminating additives, such as a conventional "sulfite" antioxidant, in the formulation that degrade the epinephrine potency, generates degradation products, and potentially causes the subsequent severe asthma and/or allergy reactions. In some embodiments, compositions provided herein reduce a patient's risk of exposure to unwanted degradation products (e.g., high ESA levels and unnecessary asthma and/or allergy reactions associated therewith), a patient's risk of exposure to drastic dosage overages and/or underages depending on the manufacture date of the product, a patient's exposure to unnecessary additives and agents, etc.

In certain embodiments provided herein are pharmaceutically acceptable compositions comprising epinephrine and any one or more excipients. In specific embodiments, compositions provided herein comprise epinephrine and a complexing agent, an antioxidant, a pH buffering agent, a chelating agent, a tonicity modifier, or any combination thereof. In more specific embodiments, provided herein are compositions comprising epinephrine and an antioxidant (e.g., cysteine, acetylcysteine, thioglycerol, or any combination thereof). In more specific embodiments, provided herein are compositions comprising epinephrine, a complexing agent (e.g., a cyclodextrin), and an antioxidant (e.g., cysteine, acetylcysteine, thioglycerol, or any combination thereof). In one embodiment, the pharmaceutical formulation comprises of epinephrine (e.g., formulated as a free base or a pharmaceutically acceptable salt thereof), a complexing agent, an antioxidant, a pH buffering agent, a chelating agent and a tonicity modifier in an aqueous based media. In another embodiment, the pharmaceutical formulation comprises of epinephrine (e.g., formulated as a free base or a pharmaceutically acceptable salt thereof), an antioxidant, a pH buffering agent, a chelating agent and a tonicity modifier in an aqueous based media.

In various embodiments, compositions provided herein are optionally formulated with any suitable epinephrine, such as the free base, conjugate acid, or a pharmaceutically acceptable salt thereof. In specific embodiments, the epinephrine utilized to formulate a composition provided herein is selected from epinephrine (free base), epinephrine bitartrate, and epinephrine hydrochloride and/or a combination thereof. Generally, compositions described herein as comprising epinephrine refer to a dissolved epinephrine, whether dissolved free base, conjugate acid, or a salt thereof. Compositions provided herein optionally comprise epinephrine in the free base form and/or in a protonated cation (conjugate acid) or salt form. In some embodiments, the epinephrine is provided in a composition herein and/or formulated into a composition herein in a free base equivalent amount of about 0.0001 wt. % to about 5 wt. %. In some instances, concentrations vary with varying therapeutic treatments and/or administration routes. In specific embodiments, compositions provided herein comprise about 0.0001 wt. % to about 1 wt. % epinephrine (e.g., for injectable formulations or topical formulations), about 0.5 wt. % to about 2 wt. % epinephrine (e.g., for ophthalmic drops), about 1 wt. % to about 5 wt. % (e.g., for inhalation formulations). In certain embodiments, the epinephrine is l-epinephrine or (−) epinephrine, such as at a concentration of about 0.01 wt. % to about 1.0 wt. %.

In some instances, provided herein is the use of cyclodextrin as a complexing agent to chemically form an inclusion complex with epinephrine. In various embodiments herein, any suitable complexing agent is optionally utilized, such as a native and/or modified cyclodextrin derivative. In specific embodiment, a cyclodextrin utilized in a formulation provided optionally includes, e.g., a α-cyclodextrin, ß-cyclodextrin, γ-cyclodextrin, modified α-cyclodexin, modified ß-cyclodextin, modified γ-cyclodextrin, and/or a combination thereof. In certain embodiments, the complexing agent is utilized in a composition herein in a molar ratio of about 1:10 to about 10:1 of cyclodextrin to epinephrine. In some embodiments, preferred cyclodextrins include, by way of non-limiting example, modified ß-cyclodextins, such as hydroxypropyl β-cyclodextrin (Kleptose® HPB, Kleptose® HP, Trappsol® HPB), sulfobutyl ether β-cyclodextrin (Captisol®), randomly methylated β-cyclodextrin (Kleptose® Crysmeb Exp), or a combination thereof. In specific embodiments, the compositions comprise and/or are formulated with a complexing agent (e.g., cyclodextrin) at a molar ratio of about 1:10 to about 2:1, such as about 1:3 to about 2:1 molar ratio, of cyclodextrin to epinephrine Cyclodextrins (sometimes called cycloamyloses) are a family of compounds made up of sugar molecules bound together in a ring (cyclic oligosaccharides). For example, sulfobutylether β-cyclodextrin (SBEßCD) is a polyanionic beta-cyclodextrin derivative with a sodium sulfonate salt separated from the lipophilic cavity by a butyl ether spacer group, or sulfobutylether. SBEßCD is not a single chemical species, but comprised of a multitude of polymeric structures of varying degrees of substitution and positional/regional isomers. SBEßCD is an approved pharmaceutical ingredient for commercial injectable products. Hydroxypropyl β-cyclodextrin (HPßCD) is the most widely used modified ß-cyclodextrin with the lipophilic cavity formed by 7 glucose units. HPßCD has the most extensive collection of safety data in the technical literature with no adverse reactions reported, and is approved for use for injectable products and parenteral products.

While not being bound by any theory, examples of association constants (K) of the inclusion complex between epinephrine and SBEßCD in aqueous solution were reported 488 M$^{-1}$ and 111 M$^{-1}$ at pH 3.5 and 5.5, respectively (US 2015/0374832 A1). The K value can be used to determine free or unbound drug in the complex solution (Rajewski, R. A. and Stella, V. J. *Pharmaceutical Applications of Cyclodextrins. 2. In Vivo Drug Delivery*, Journal of Pharmaceutical Sciences, 85(11), 1142-1169, 1996) as shown in Equation 1.

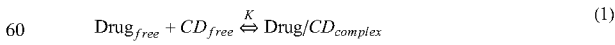

$$\text{Drug}_{free} + CD_{free} \overset{K}{\Leftrightarrow} \text{Drug}/CD_{complex} \quad (1)$$

where CD is cyclodextrin. The total solubility of epinephrine, a weakly basic drug in a presence of CD at a low pH range can be described in Equation 2.

$$S_{Total} = S_0 + S_{ionic} + S_{Complex} \quad (2)$$

where $S_{total}$ is total drug solubility, $S_0$ is an intrinsic solubility of drug, $S_{ionic}$ is an ionization solubility of drug, and $S_{Complex}$ is a complex solubility of drug-CD. Equation 2 can also be described in Equation 3.

$$S_{total} = S_0 + S_{ionic} + \frac{K[S_0 + S_{ionic}][CD_{total}]}{K[S_0 + S_{ionic}] + 1} \quad (3)$$

where $[CD_{total}]$ is total cyclodextrin added to the solution, and K is 1:1 association constant defined by Equation 4.

$$K = \frac{[Drug - CD_{complex}]}{[Drug_{free}][CD_{free}]} \quad (4)$$

Since $S_{ionic} >>> S_0$, therefore $S_0 + S_{ionic} \approx S_{ionic}$ and Equation 3 can be rewritten by Equation 5.

$$S_{total} = S_{ionic} + \frac{K[S_{ionic}][CD_{total}]}{K[S_{ionic}] + 1} \quad (5)$$

The fraction of epinephrine in the formulation that would be in complex with CD at any once instance as determined by Equation 5 is shown in FIG. 1. This data demonstrates that epinephrine is expected to weakly complex with SBEβCD at lower pH—where in general, the K values of any drug and CD complex of 10 to $1 \times 10^3$ M$^{-1}$ are common, values of $1 \times 10^4$ M$^{-1}$ are seen occasionally, and values $>1 \times 10^5$ M$^{-1}$ are unusual (Stella V. J. and He Q., Cyclodextrins, Toxicologic Pathology, 36(1), 30-42, 2008).

Generally, this is an important mechanism as the free drug should be immediately released from the complex after injection in order to provide its pharmacological effect. In some instances provided herein, the drug is easily released with a minimum dilution of body aqueous fluid like blood upon intramuscular or subcutaneous injection. In one illustrative example, an injection of 0.3 mL epinephrine (1:1000) in a presence of 1:2 molar ratio of SBEβCD to drug at pH 3.5 (K=488 M$^{-1}$) would rapidly release 90% and 99% free drug approximately after the dilutions with 3 mL (10×) and 30 mL (100×) body aqueous fluid, respectively as summarized in TABLE 1. A similar exercise may be performed for a 0.15 mL epinephrine injection of the same above formulation for the pediatric patient where the free drug would be rapidly released ~90% and ~99% after the dilutions with 1.5 mL (10×) and 15 mL (100×) body aqueous fluid, respectively (TABLE 1). This conservative example assumes fixed volumes, which of course is not the case in-vivo where the drug is rapidly diffused from the injection site.

TABLE 1

An example of free epinephrine released from 0.15 and 0.3 mL injection of drug complex (1:1000) containing 1:2 molar ratio of SBEβCD to drug at pH 3.5 (K = 488 M$^{-1}$).

| Time (×) | Dilution | | % Drug Complex | % Free Drug |
|---|---|---|---|---|
| | Volume (mL) | | | |
| 1 | 0.3* | 0.15** | 26.7 | 73.3 |
| 10 | 3 | 1.5 | 9.5 | 90.5 |
| 100 | 30 | 15 | 1.3 | 98.7 |
| 1000 | 300 | 150 | 0.1 | 99.9 |

*Injection volume for adult patient,
**Injection volume for pediatric patient

However, the fraction of non-complex free drug is still susceptible to the oxidation that could cause the solution discoloration due to a weak association constant (K) of epinephrine complex. In some embodiments, compositions further comprise a "non-sulfite" antioxidant, e.g., to protect the non-complexed free drug in the formulation from the oxidation.

Unexpectedly, a new discovery of antioxidant (e.g., cysteine) level in the present invention that efficiently inhibit drug oxidation and minimize the cross reaction with drug was found at very low concentrations. Indeed, low concentrations of antioxidant (e.g., cysteine) and low weight ratios of antioxidant to drug are demonstrated herein to provide dramatically improved physiochemical stability (improved potency, reduced degradation products, and improved color profile) over time, relative to both compositions lacking antioxidant (e.g., cysteine) and compositions with higher amounts of antioxidant (e.g., cysteine).

In various embodiments, a composition provided herein comprises any suitable "non-sulfite" antioxidant (including a single antioxidant or a combination of antioxidants). In specific embodiments, "non-sulfite" antioxidants include by way of non-limiting example oxine, boric acid, borate, ascorbic acid, erythorbic acid, malic acid, acetylcysteine (N-acetylcysteine or N-acetyl-L-cysteine), thioglycerol (monothioglycerol or 1-thioglycerol), cysteine (L-cysteine), cysteine hydrochloride, citric acid, polyvinylpyrrolidone and/or any combination (of two or more) thereof. In specific embodiments, antioxidants are included in an amount of about 0.001 wt. % to about 2.6 wt. %, e.g., about 0.001 wt. % to about 0.1, about 0.001 wt. % to about 0.05 wt. %, about 0.005 wt. % to about 0.05 wt. %, about 0.001 wt. % to about 0.02 wt. %, or the like. In some embodiments, antioxidant (comprising one or more antioxidant, such as cysteine, acetylcysteine, thioglycerol, or any combination (of two or more) thereof) is present in an amount of about 0.005 wt. % to about 0.07 wt. %. In specific embodiments, antioxidant is present in an amount of about 0.01 wt. % to about 0.07 wt. %. In some embodiments, antioxidant is present in an amount of about 0.005 wt. % to about 0.05 wt. %. In specific embodiments, antioxidant is present in an amount of about 0.01 wt. % to about 0.05 wt. %. In some embodiments, antioxidant is present in an amount of about 0.015 wt. % to about 0.07 wt. %. In specific embodiments, antioxidant is present in an amount of about 0.015 wt. % to about 0.05 wt. %. In more specific embodiments, the antioxidant is present in an amount of about 0.02 wt. % to about 0.04 wt. %, such as about 0.03 wt. %.

In specific embodiments, a composition herein comprises cysteine (e.g., as the antioxidant), such as having a concentration of about 0.005 wt. % to about 0.05 wt. % (e.g., about 0.01 wt. % to about 0.04 wt. %). In some embodiments, a composition herein comprises thioglycerol (e.g., as the antioxidant), such as having a concentration of about 0.005 wt. % to about 0.07 wt. %. In some embodiments, a composition herein comprises acetylcysteine (e.g., as the antioxidant), such as having a concentration of about 0.005 wt. % to about 0.07 wt. %. In certain embodiments, the antioxidant comprises cysteine and acetylcysteine. In other embodiments, the antioxidant comprises cysteine and thioglycerol. In still other embodiments, the antioxidant comprises acetylcysteine and thioglycerol.

In further or alternative embodiments, a weight ratio of antioxidant (e.g., cysteine) to drug is less than 1:1, such as about 1:20 to about 1:2, e.g., about 1:20 to about 1:5, or the like. In specific embodiments, the weight ratio is about 1:20 to about 1:1, about 1:20 to about 7:10, about 1:20 to about 1:2, about 1:20 to about 3:10, about 1:10 to about 1:1, about 1:10 to about 7:10, about 1:10 to about 1:2, about 1:10 to about 3:10, or the like.

In some embodiments, the weight ratio of antioxidant (e.g., cysteine, acetylcysteine, thioglycerol, or any combination thereof) to drug is about 7:10 or less (e.g., about 1:2 or less, about 7:20 or less, about 3:10 or less, or about 1:5 or less). In some embodiments, the ratio of antioxidant to drug is about 1:20 or more (e.g., up to an upper limit described above), or about 1:10 or more, about 1:7 or more, about 1:5 or more, or the like. In certain embodiments, the weight ratio of antioxidant to drug is about 1:20 to about 7:10 (e.g., about 1:10 to about 7:10, or about 1:10 to about 5:10). In specific embodiments, the weight ratio of antioxidant-to-epinephrine is about 2:10 to about 4:10 (e.g., about 3:10).

In certain embodiments, antioxidants are provided in the composition in an amount as described herein, such as about 0.05 mg/mL to less than 1 mg/mL, about 0.05 mg/mL to about 0.7 mg/mL, about 0.05 to about 0.5 mg/mL, about 0.05 mg/mL to about 0.35 mg/mL, about 0.05 mg/mL to about 0.3 mg/mL, about 0.1 mg/mL to less than 1 mg/mL, about 0.1 mg/mL to about 0.7 mg/mL, about 0.1 mg/mL to about 0.5 mg/mL, about 0.1 mg/mL to about 0.35 mg/mL, or about 0.1 mg/mL to about 0.3 mg/mL.

In some instances, pH maintenance is an important contributor to the rate of release of active from a complexing agent (e.g., as relating the K value discussed herein). In certain embodiments, a buffering agent is utilized, such as to maintain the pH within the target range. In some embodiments, such as wherein a complexing agent is omitted, the buffering agent is optionally omitted. The buffering agent formulated into a composition herein can be any suitable agent. In specific embodiments, the buffering agent is or comprises, by way of non-limiting example, acetic acid, acetate (e.g., formulated with sodium acetate, sodium acetate anhydrous), ascorbic acid, ascorbate (e.g., formulated with sodium ascorbate), benzoic acid, benzyl benzoic acid, benzyl benzoate, benzoate (e.g., formulated with sodium benzoate), benzenesulfonic acid, citric acid (e.g., formulated with citric acid (anhydrous), citric acid (monohydrate)), citrate (e.g., formulated with sodium citrate, disodium citrate (sesquihydrate), disodium hydrogen citrate, trisodium citrate (anhydrous), or trisodium citrate (dihydrate)), maleic acid, methanesulfonic acid, phosphoric acid, metaphosphoric acid, phosphate (e.g., formulated with potassium phosphate (monobasic), potassium phosphate (dibasic), sodium phosphate, sodium phosphate (dibasic), sodium phosphate (dibasic, anhydrous), sodium phosphate (dibasic, heptahydrate), sodium phosphate (monobasic), sodium phosphate (monobasic anhydrous), sodium phosphate (monobasic, monohydrate), or sodium phosphate (monobasic, dihydrate)), succinic acid, succinate (e.g., formulated with sodium succinate, or sodium succinate hexahydrate), tartaric acid, tartarate (e.g., formulated with sodium tartarate), and/or a combination thereof. It is to be understood that a composition provided herein and formulated with such a composition may comprise the buffering agent as is, or as a conjugate acid or base thereof (e.g., a composition formulated with citric acid may comprise citric acid and/or citrate at varying concentrations depending on the pH of the composition). In certain embodiments, a composition provided herein comprises 0.001 wt. % to about 2 wt. % (e.g., about 0.001 wt. % to about 1 wt. %, about 0.001 wt. % to about 0.01 wt. %, about 0.001 wt. % to about 0.02 wt. %, about 0.001 wt. % to about 0.05 wt. %, or the like) buffering agent (e.g., based on combined weight of conjugate acid and base thereof). In specific embodiments, of the composition comprises about 0.005 wt. % to about 0.05 wt. %. In further or alternative embodiments, the weight ratio of buffering agent (e.g., citric acid/citrate) to drug is about 1:20 to about 1:2, such as about 1:20 to about 1:5, about 1:10 to about 1:2, about 1:10 to about 1:5, or the like.

In some embodiments, a composition provided herein comprises a chelating agent, such as to further reduce epinephrine degradation, e.g., due to the presence of any trace metallic catalyst. Any suitable chelating agent is optionally utilized. In specific embodiments, the chelating agent is, by way of non-limiting example, edetate. In various embodiments, edetate is ethylenediaminetetraacetic acid, or an anion (e.g., $-1$, $-2$, $-3$, or $-4$ anion), solvate, or salt thereof, such as a compound represented by the formula: $(ROOCCH_2)_2NCH_2CH_2N(CH_2COOR)_2$, wherein each R is independently H or a negative charge (which negative charge may be in association with a cationic species, such as $Na^+$, $Ca^{2+}$, $H_3O^+$, or the like). In various embodiments herein, compositions comprising edetate are formulating using ethylenediaminetetraacetic acid or a pharmaceutically acceptable salt thereof, such as, by way of non-limiting example, calcium disodium, edetate disodium, edetate disodium anhydrous, edetate sodium, edetate disodium dehydrate, edetate tetrasodium, and/or a combination thereof. In some embodiments, chelating agent (e.g., edetate) is utilized in an amount of about 0.001 wt % to about 1 wt. %. In specific embodiments, edetate disodium is utilized to formulation a composition herein. In further or alternative embodiments, chelating agent (e.g., edetate, such as formulated with edetate disodium) is utilized in an amount of about 0.001 wt. % to about 0.05 wt. % (e.g., about 0.005 wt. % to about 0.05 wt. %, about 0.005 wt. % to about 0.01 wt. %, or the like). In some embodiments, the weight ratio of chelating agent (e.g. edetate—e.g., using edetate disodium in formulating) to epinephrine is about 1:20 to about 1:2.

In some embodiments, water suitable for injection (WFI) is utilized as an aqueous diluent. In some instances, the pH of WFI is adjusted to effectively enhance the physicochemical stability of epinephrine complex formulation (e.g., using hydrochloric acid and/or sodium hydroxide) to a specific range of pH 2-5 (e.g., about pH 2.5, about pH 3.5, about pH 2.5 to about pH 3.5, or the like).

In some embodiments, a tonicity modifier is utilized to adjust the solution osmolality within a body physiological range. Any suitable tonicity modifier is optionally utilized, such as, by way of non-limiting example, sodium chloride and/or dextrose or a combination thereof. In specific embodiments, sodium chloride is utilized (dissolved/disassociated sodium chloride being present in a composition herein). In specific embodiments, a tonicity modifier is used to provide the solution osmolality within a range of about 200-400 mOsm/kg.

In another embodiment, epinephrine complex and non-complex formulations is used in a conjunction with an administrative device. Any suitable device is utilized. In specific embodiments, the device is, by way of non-limiting example, a pre-filled syringe or cartridge with or without the auto injector for both manual and auto injections. In some instances, such devices are calibrated and/or configured to precisely and accurately deliver effective amount of epinephrine medication.

In another embodiment, epinephrine complex and non-complex formulations can be used for treating anaphylactic shock by administrating epinephrine formulation to patients via intramuscular injection or subcutaneous injection or intravenous injection.

It is to be understood that any reference to a composition comprising an associate compound described herein (e.g., a salt or an acid) includes a composition comprising disassociated and/or solvated forms of that compound (e.g., ions of a salt and/or conjugate base of an acid).

The following non-limiting examples are provided to further explain and illustrate the invention.

EXAMPLES

Pharmaceutical formulations are prepared by mixing cyclodextrin, edetate, citric acid, cysteine, and sodium chloride into a pH 2.0 WFI prior to adding and mixing epinephrine. Adjust formulation pH to the target pH using HCl and/or NaOH solutions. Adjust the final volume using a target pH WFI. Examples 1-10 are prepared using this procedure.

Example 1

| Ingredient | Concentration (mg/mL) |
|---|---|
| Epinephrine (as free base) | 1.0 |
| SBEβCD | 6.0 |
| Cysteine | 5.0 |
| Citric Acid | 5.0 |
| Edetate | 2.0 |
| Sodium Chloride | 7.8 |
| HCl and/or NaOH (pH 2.5 ± 0.1) | q.s. |
| Water for Injection (WFI) | q.s. |

Example 2

| Ingredient | Concentration (mg/mL) |
|---|---|
| Epinephrine (as free base) | 1.0 |
| SBEβCD | 6.0 |
| Cysteine | 5.0 |
| Citric Acid | 5.0 |
| Edetate | 2.0 |
| Sodium Chloride | 7.8 |
| HCl and/or NaOH (pH 3.5 ± 0.1) | q.s. |
| Water for Injection (WFI) | q.s. |

Example 3

| Ingredient | Concentration (mg/mL) |
|---|---|
| Epinephrine (as free base) | 1.0 |
| HPβCD | 4.0 |
| Cysteine | 5.0 |
| Citric Acid | 5.0 |
| Edetate | 2.0 |
| Sodium Chloride | 7.8 |
| HCl and/or NaOH (pH 2.5 ± 0.1) | q.s. |
| Water for Injection (WFI) | q.s. |

Example 4

| Ingredient | Concentration (mg/mL) |
|---|---|
| Epinephrine (as free base) | 1.0 |
| HPβCD | 4.0 |
| Cysteine | 5.0 |
| Citric Acid | 5.0 |
| Edetate | 2.0 |
| Sodium Chloride | 7.8 |
| HCl and/or NaOH (pH 3.5 ± 0.1) | q.s. |
| Water for Injection (WFI) | q.s. |

Example 5

| Ingredient | Concentration (mg/mL) |
|---|---|
| Epinephrine (as free base) | 1.0 |
| SBEβCD | 6.0 |
| Cysteine | 2.0 |
| Citric Acid | 2.0 |
| Edetate | 0.2 |
| Sodium Chloride | 7.8 |
| HCl and/or NaOH (pH 3.5 ± 0.1) | q.s. |
| Water for Injection (WFI) | q.s. |

Example 6

| Ingredient | Concentration (mg/mL) |
|---|---|
| Epinephrine (as free base) | 1.0 |
| HPβCD | 4.0 |
| Cysteine | 2.0 |
| Citric Acid | 2.0 |
| Edetate | 0.2 |
| Sodium Chloride | 7.8 |
| HCl and/or NaOH (pH 3.5 ± 0.1) | q.s. |
| Water for Injection (WFI) | q.s. |

Example 7

| Ingredient | Concentration (mg/mL) |
| --- | --- |
| Epinephrine (as free base) | 1.0 |
| SBEβCD | 6.0 |
| Cysteine | 1.0 |
| Citric Acid | 1.0 |
| Edetate | 0.1 |
| Sodium Chloride | 7.8 |
| HCl and/or NaOH (pH 2.5 ± 0.1) | q.s. |
| Water for Injection (WFI) | q.s. |

Example 8

| Ingredient | Concentration (mg/mL) |
| --- | --- |
| Epinephrine (as free base) | 1.0 |
| HPβCD | 4.0 |
| Cysteine | 1.0 |
| Citric Acid | 1.0 |
| Edetate | 0.1 |
| Sodium Chloride | 7.8 |
| HCl and/or NaOH (pH 2.5 ± 0.1) | q.s. |
| Water for Injection (WFI) | q.s. |

Example 9

| Ingredient | Concentration (mg/mL) |
| --- | --- |
| Epinephrine (as free base) | 1.0 |
| SBEβCD | 6.0 |
| Cysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 10

| Ingredient | Concentration (mg/mL) |
| --- | --- |
| Epinephrine (as free base) | 1.0 |
| HPβCD | 4.0 |
| Cysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

The method of preparing non-complex formulations and using an antioxidant in Examples 11-15 is carried out by mixing edetate, citric acid, cysteine, and sodium chloride into a pH 2.0 WFI prior to adding and mixing epinephrine. Adjust formulation pH to the target pH using HCl and/or NaOH solutions. Adjust the final volume using a target pH WFI.

Example 11

| Ingredient | Concentration (mg/mL) |
| --- | --- |
| Epinephrine (as free base) | 1.0 |
| Cysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 12

| Ingredient | Concentration (mg/mL) |
| --- | --- |
| Epinephrine (as free base) | 1.0 |
| Cysteine | 0.3 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 13

| Ingredient | Concentration (mg/mL) |
| --- | --- |
| Epinephrine (as free base) | 1.0 |
| Cysteine | 0.5 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 14

| Ingredient | Concentration (mg/mL) |
| --- | --- |
| Epinephrine (as free base) | 1.0 |
| Cysteine | 0.7 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 15

| Ingredient | Concentration (mg/mL) |
| --- | --- |
| Epinephrine (as free base) | 1.0 |
| Cysteine | 1.0 |
| Citric Acid | 0.1 |

-continued

| Ingredient | Concentration (mg/mL) |
|---|---|
| Edetate | 0.1 |
| Sodium Chloride | 7.8 |
| HCl and/or NaOH (pH 2.5 ± 0.1) | q.s. |
| Water for Injection (WFI) | q.s. |

The method of preparing non-complex formulation and using an antioxidant in Examples 16-20 is carried out by mixing edetate, citric acid, thioglycerol, and sodium chloride into a pH 2.0 WFI prior to adding and mixing epinephrine. Adjust formulation pH to the target pH using HCl and/or NaOH solutions. Adjust the final volume using a target pH WFI.

Example 16

| Ingredient | Concentration (mg/mL) |
|---|---|
| Epinephrine (as free base) | 1.0 |
| Thioglycerol | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 17

| Ingredient | Concentration (mg/mL) |
|---|---|
| Epinephrine (as free base) | 1.0 |
| Thioglycerol | 0.3 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 18

| Ingredient | Concentration (mg/mL) |
|---|---|
| Epinephrine (as free base) | 1.0 |
| Thioglycerol | 0.5 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 19

| Ingredient | Concentration (mg/mL) |
|---|---|
| Epinephrine (as free base) | 1.0 |
| Thioglycerol | 0.7 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 20

| Ingredient | Concentration (mg/mL) |
|---|---|
| Epinephrine (as free base) | 1.0 |
| Thioglycerol | 1.0 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

The method of preparing non-complex formulations and using an antioxidant in Examples 21-25 is carried out by mixing edetate, citric acid, acetylcysteine, and sodium chloride into a pH 2.0 WFI prior to adding and mixing epinephrine. Adjust formulation pH to the target pH using HCl and/or NaOH solutions. Adjust the final volume using a target pH WFI.

Example 21

| Ingredient | Concentration (mg/mL) |
|---|---|
| Epinephrine (as free base) | 1.0 |
| Acetylcysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 22

| Ingredient | Concentration (mg/mL) |
|---|---|
| Epinephrine (as free base) | 1.0 |
| Acetylcysteine | 0.3 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 23

| Ingredient | Concentration (mg/mL) |
| --- | --- |
| Epinephrine (as free base) | 1.0 |
| Acetylcysteine | 0.5 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 24

| Ingredient | Concentration (mg/mL) |
| --- | --- |
| Epinephrine (as free base) | 1.0 |
| Acetylcysteine | 0.7 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 25

| Ingredient | Concentration (mg/mL) |
| --- | --- |
| Epinephrine (as free base) | 1.0 |
| Acetylcysteine | 1.0 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

The method of preparing non-complex formulations and using mixed antioxidants in Examples 26-28 is carried out by mixing edetate, citric acid, antioxidants (i.e. cysteine, thioglycerol and acetylcysteine) and sodium chloride into a pH 2.0 WFI prior to adding and mixing epinephrine. Adjust formulation pH to the target pH using HCl and/or NaOH solutions. Adjust the final volume using a target pH WFI.

Example 26

| Ingredient | Concentration (mg/mL) |
| --- | --- |
| Epinephrine (as free base) | 1.0 |
| Cysteine | 0.1 |
| Thioglycerol | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 27

| Ingredient | Concentration (mg/mL) |
| --- | --- |
| Epinephrine (as free base) | 1.0 |
| Cysteine | 0.1 |
| Acetylcysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 28

| Ingredient | Concentration (mg/mL) |
| --- | --- |
| Epinephrine (as free base) | 1.0 |
| Thioglycerol | 0.1 |
| Acetylcysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |
| Water for Injection (WFI) | q.s. |

The method of preparing non-complex pediatric formulations in Examples 29-32 is carried out by mixing edetate, citric acid, antioxidants (i.e. cysteine, thioglycerol and acetylcysteine) and sodium chloride into a pH 2.0 WFI prior to adding and mixing epinephrine. Adjust formulation pH to the target pH using HCl and/or NaOH solutions. Adjust the final volume using a target pH WFI.

Example 29

| Ingredient | Concentration (mg/mL) |
| --- | --- |
| Epinephrine (as free base) | 0.5 |
| Cysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 30

| Ingredient | Concentration (mg/mL) |
| --- | --- |
| Epinephrine (as free base) | 0.5 |
| Cysteine | 0.1 |
| Thioglycerol | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 31

| Ingredient | Concentration (mg/mL) |
| --- | --- |
| Epinephrine (as free base) | 0.5 |
| Cysteine | 0.1 |
| Acetylcysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 32

| Ingredient | Concentration (mg/mL) |
| --- | --- |
| Epinephrine (as free base) | 0.5 |
| Thioglycerol | 0.1 |
| Acetylcysteine | 0.1 |
| Citric Acid | 0.1 |
| Edetate | 0.1 |
| Sodium Chloride | 7.8 |
| HCl and/or NaOH (pH 2.5 ± 0.1) | q.s. |
| Water for Injection (WFI) | q.s. |

Example 33

The method of preparing a typical commercial "sulfite" formulation in Examples 33 was carried out by mixing sodium chloride and sodium bisulfite into a pH 2.2 WFI prior to adding and mixing epinephrine. Adjust formulation pH to the target pH using HCl and/or NaOH solutions. Adjust the final volume using a target pH WFI.

| Ingredient | Concentration (mg/mL) |
| --- | --- |
| Epinephrine (as free base) | 1.0 |
| Sodium Bisulfite | 1.5 |
| Sodium Chloride | 8.5 |
| HCl and/or NaOH (pH 3.5 ± 0.1) | q.s. |
| Water for Injection (WFI) | q.s. |

All epinephrine formulation candidates were tested for drug potency, pH and appearance of coloration and precipitation. Selected samples were also tested for drug chirality. The potency and chirality of drug were analyzed using HPLC methods. The degree of coloration was visually inspected and analytically measured their optical densities using a UV/VIS spectrophotometer at the maximum absorption wavelength ($\lambda$max) at 485 nm. Iodine solution (0.0005 N) in water was used as a reference standard to confirm the instrument read-out consistency.

Surprisingly, as illustrated in TABLES 2-4, after 1 month storage at 50° C., substantial drug degradations were observed in samples having cysteine levels of 0.1 wt. % to 0.5 wt. % or 1:1 to 5:1 weight ratio of cysteine-to-drug (compositions of Examples 1-8).

At 5:1 weight ratio of cysteine-to-drug, epinephrine in both SBEßCD and HPßCD formulations was rapidly degraded in the same fashion to be ~67% (Examples 1 and 3) and ~86-90% (Examples 2 and 4) at pHs 2.5 and 3.5, respectively as shown in TABLE 2. The appearances of precipitation and slight discoloration were similarly observed in both complex formulations at pH 2.5 and 3.5, respectively (TABLE 2).

TABLE 2

Stabilities of epinephrine complex formulations containing about 0.5 wt. % antioxidant (cysteine) (5:1 weight ratio of cysteine-to-drug) after 1 month storage at 50° C.

| Example | CD | Potency (%) | pH | Appearance | O.D. |
| --- | --- | --- | --- | --- | --- |
| 1 | SBEßCD | 66.5 | 2.6 | Colorless & precipitation | 0.0039 |
| 2 | SBEßCD | 86.0 | 3.5 | Slightly light tan | 0.0086 |
| 3 | HPßCD | 67.4 | 2.6 | Colorless & precipitation | 0.0057 |
| 4 | HPßCD | 89.5 | 3.6 | Slightly light tan | 0.0086 |
| NA | 0.0005N Iodine | NA | NA | Slightly brownish | 0.1290 |

ND = Not detected;
NA = Not Applicable;
O.D. = Optical density (Absorbance at $\lambda$max = 485 nm)

At 2:1 weight ratio of cysteine-to-drug (Examples 5 and 6), epinephrine degradations in both complex formulations at pH 3.5 were found to be ~87-93% and comparable to that (~86-90%) at 5:1 weight ratio (Examples 2 and 4) and same pH condition as shown in TABLE 3. The appearances of both formulations were "clear, colorless & no particulates".

TABLE 3

Stabilities of epinephrine complex formulations containing about 0.2 wt. % antioxidant (cysteine) (2:1 weight ratio of cysteine-to-drug) after 1 month storage at 50° C.

| Example | CD | Potency (%) | pH | Appearance | O.D. |
| --- | --- | --- | --- | --- | --- |
| 5 | SBEßCD | 87.1 | 3.4 | Clear, colorless & no particulates | 0.0142 |
| 6 | HPßCD | 92.9 | 3.5 | Clear, colorless & no particulates | 0.0024 |
| NA | 0.0005N Iodine | NA | NA | Slightly brownish | 0.1206 |

ND = Not detected;
NA = Not Applicable;
O.D. = Optical density (Absorbance at $\lambda$max = 485 nm)

At 1:1 weight ratio of cysteine-to-drug (Examples 7 and 8), epinephrine degradations in both complex formulations at pH 2.5 were found to be ~85-92% with some improvements over that (~67%) at 5:1 weight ratio (Examples 1 and 3) and same pH condition as shown in TABLE 4. The appearances of both formulations were "clear, colorless & no particulates".

TABLE 4

Stabilities of epinephrine complex formulations containing about 0.1 wt. % antioxidant (cysteine) (1:1 weight ratio of cysteine-to-drug) at after 1 month storage at 50° C.

| Example | CD | Potency (%) | pH | Appearance | O.D. |
|---|---|---|---|---|---|
| 7 | SBEβCD | 85.3 | 2.5 | Clear, colorless & no particulates | 0.0146 |
| 8 | HPβCD | 91.7 | 2.5 | Clear, colorless & no particulates | 0.0018 |
| NA | 0.0005N Iodine | NA | NA | Slightly brownish | 0.1206 |

ND = Not detected;
NA = Not Applicable;
O.D. = Optical density (Absorbance at λmax = 485 nm)

Figure 2:
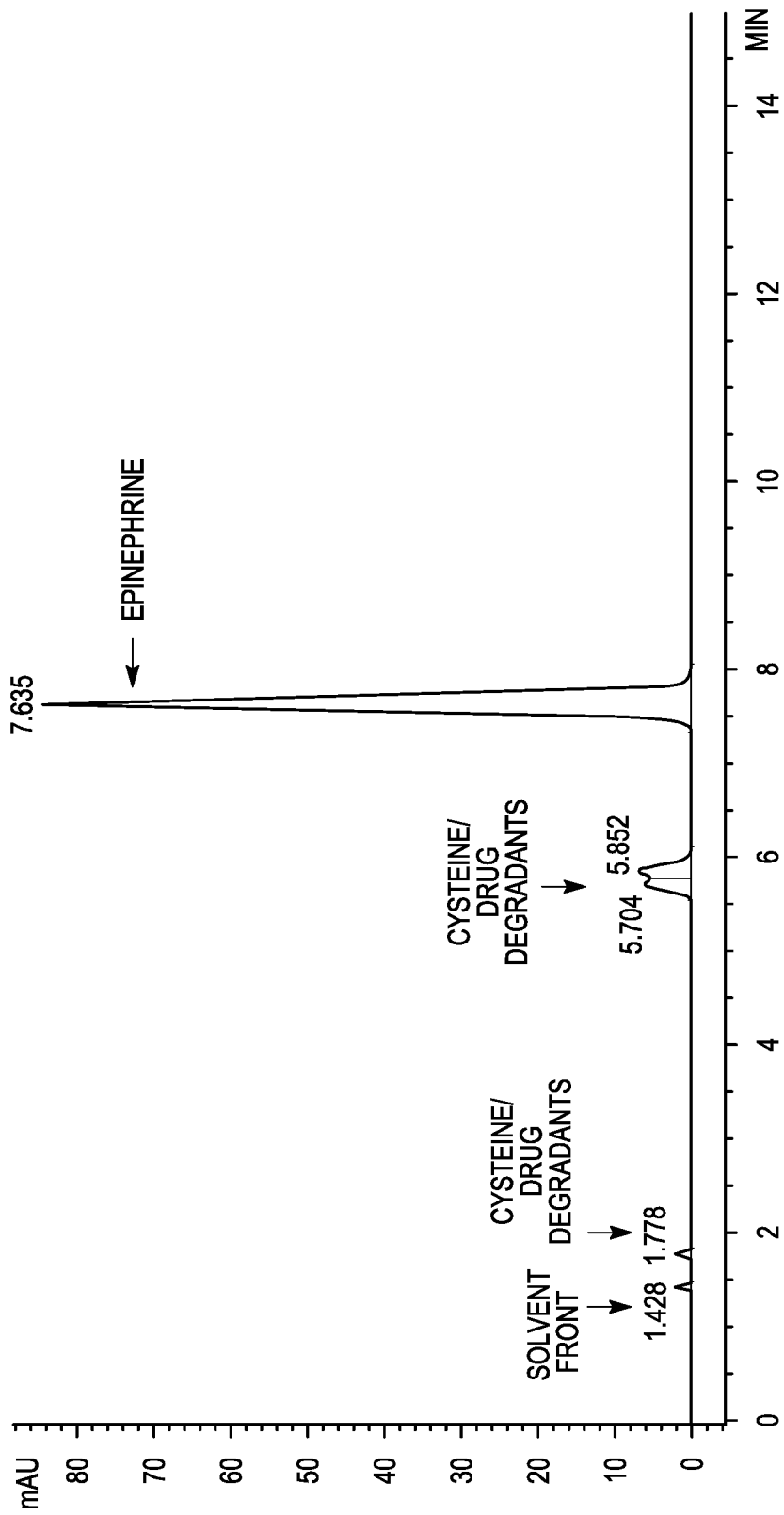
FIG. 2 illustrates an HPLC chromatogram of epinephrine degradation in a presence of 1:1 weight ratio of cysteine-to-drug at pH 2.5 after 1 month at 50° C.

As demonstrated in FIG. 2, an example of HPLC chromatogram of related degradants were observed ~11.2% (peak area) in an epinephrine solution containing 0.1 wt. % cysteine or 1:1 weight ratio of cysteine-to-drug at pH 2.5 (Example 15) after 1 month storage at 50° C.

Unexpectedly, at lower antioxidant (cysteine) levels (e.g., below 0.1 wt. % or lower than 1:1 weight ratio of antioxidant (cysteine)-to-drug), degradation of epinephrine actually decreased. For instance at 0.01 wt. % cysteine or 1:10 weight ratio of cysteine-to-drug, an excellent improvement of physicochemical stability of epinephrine in both complex formulations (Examples 9 and 10) were discovered to remain ~100% drug potency after 1 month storage at 50° C. as shown in TABLE 5.

A typical commercial "sulfite" formulation (Example 33) was also studied and compared as a benchmark for physicochemical improvements of "sulfite free" formulations. After 1 month storage at 50° C., drug potency in commercial formulation rapidly degraded to be ~74% compared to ~100% of that in both SBEßCD and HPßCD formulations. The degradation products in the commercial formulation mainly epinephrine sulfonic acid (ESA) was found >37% compared to "not detected" levels in both formulations. The appearances of both complex formulations were observed to be "clear, colorless & no particulates" compared to a discoloration of "slightly brownish-tan" of that from the commercial one. The testing results are summarized and compared in TABLE 5.

Figure 3:
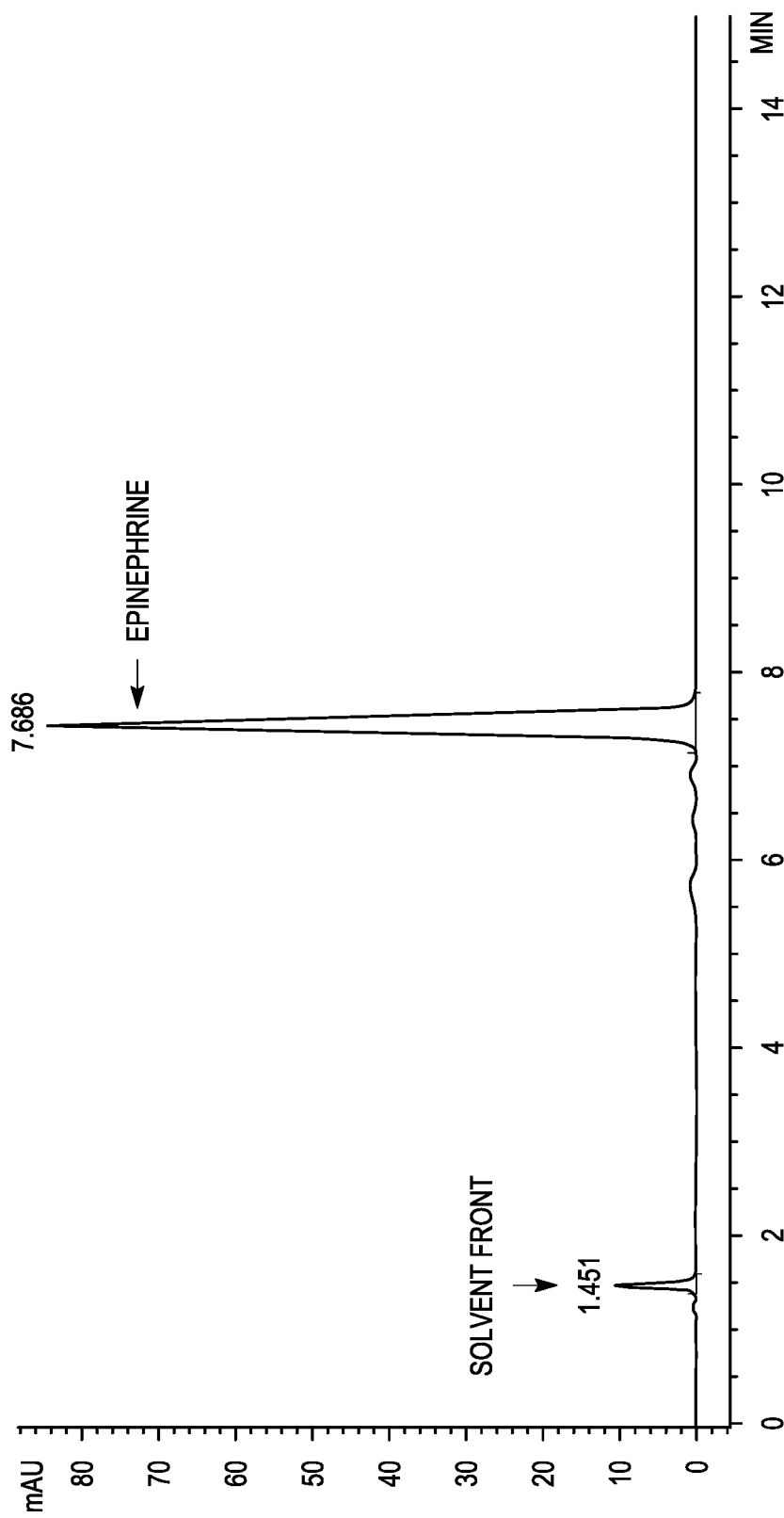
FIG. 3 illustrates an HPLC chromatogram of epinephrine stability in SBEßCD formulation containing 1:10 weight ratio of cysteine-to-drug after 1 month at 50° C.
Figure 4:
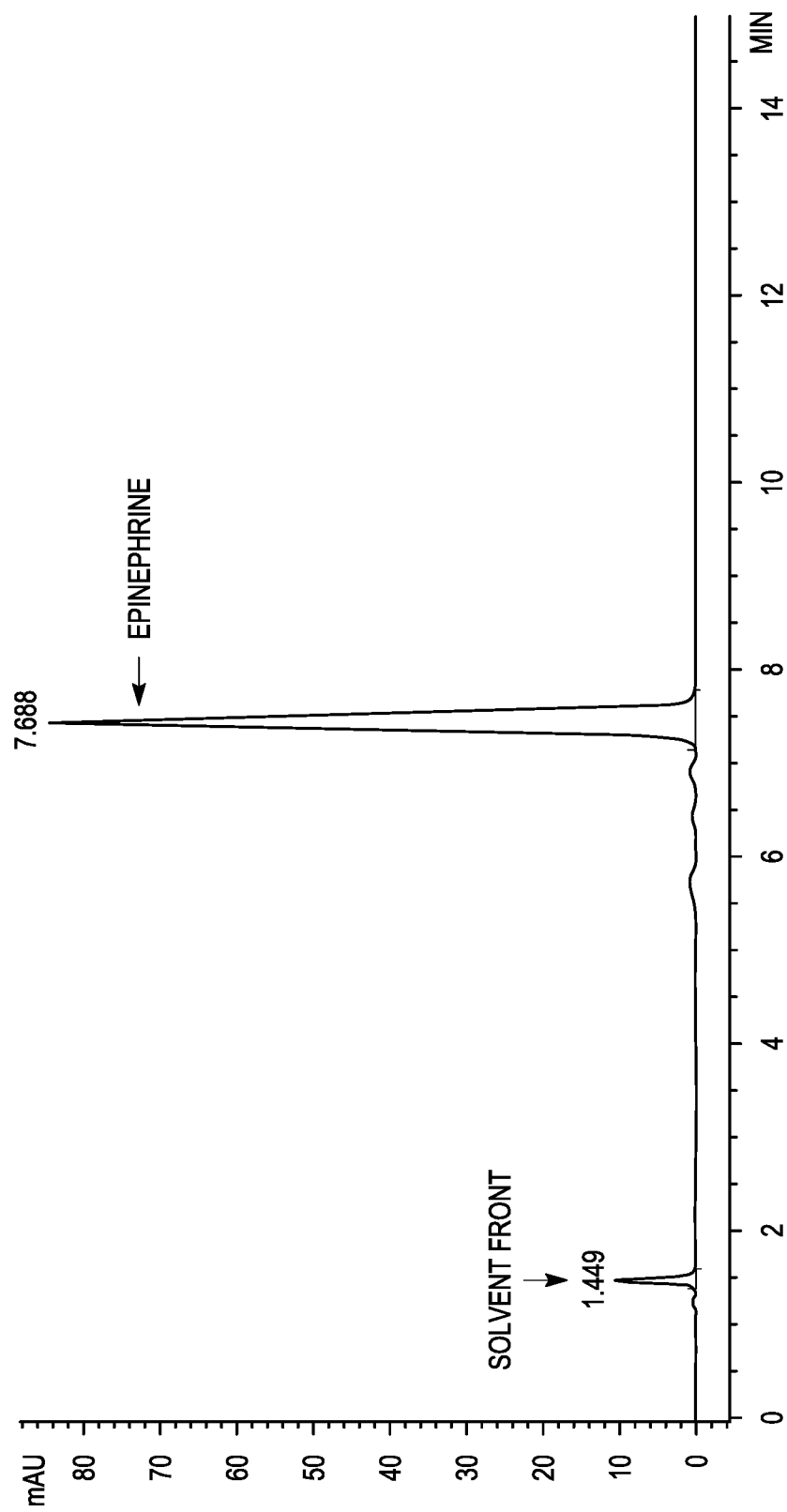
FIG. 4 illustrates an HPLC chromatogram of epinephrine stability in HPßCD formulation containing 1:10 weight ratio of cysteine-to-drug after 1 month at 50° C.
Figure 5:
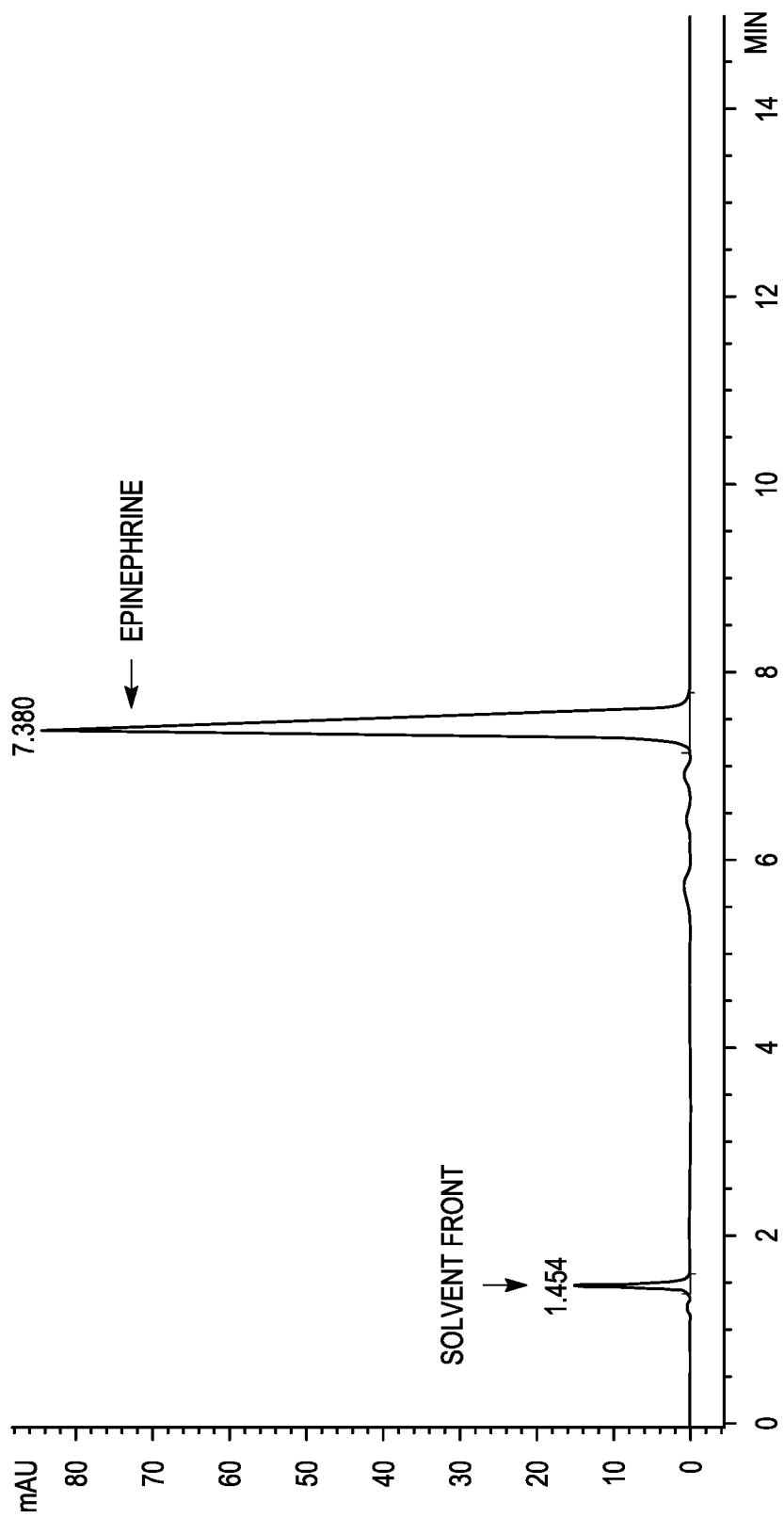
FIG. 5 illustrates an HPLC chromatogram of epinephrine stability in non-complex formulation containing 1:10 weight ratio of cysteine-to-drug after 1 month at 50° C.
Figure 6:
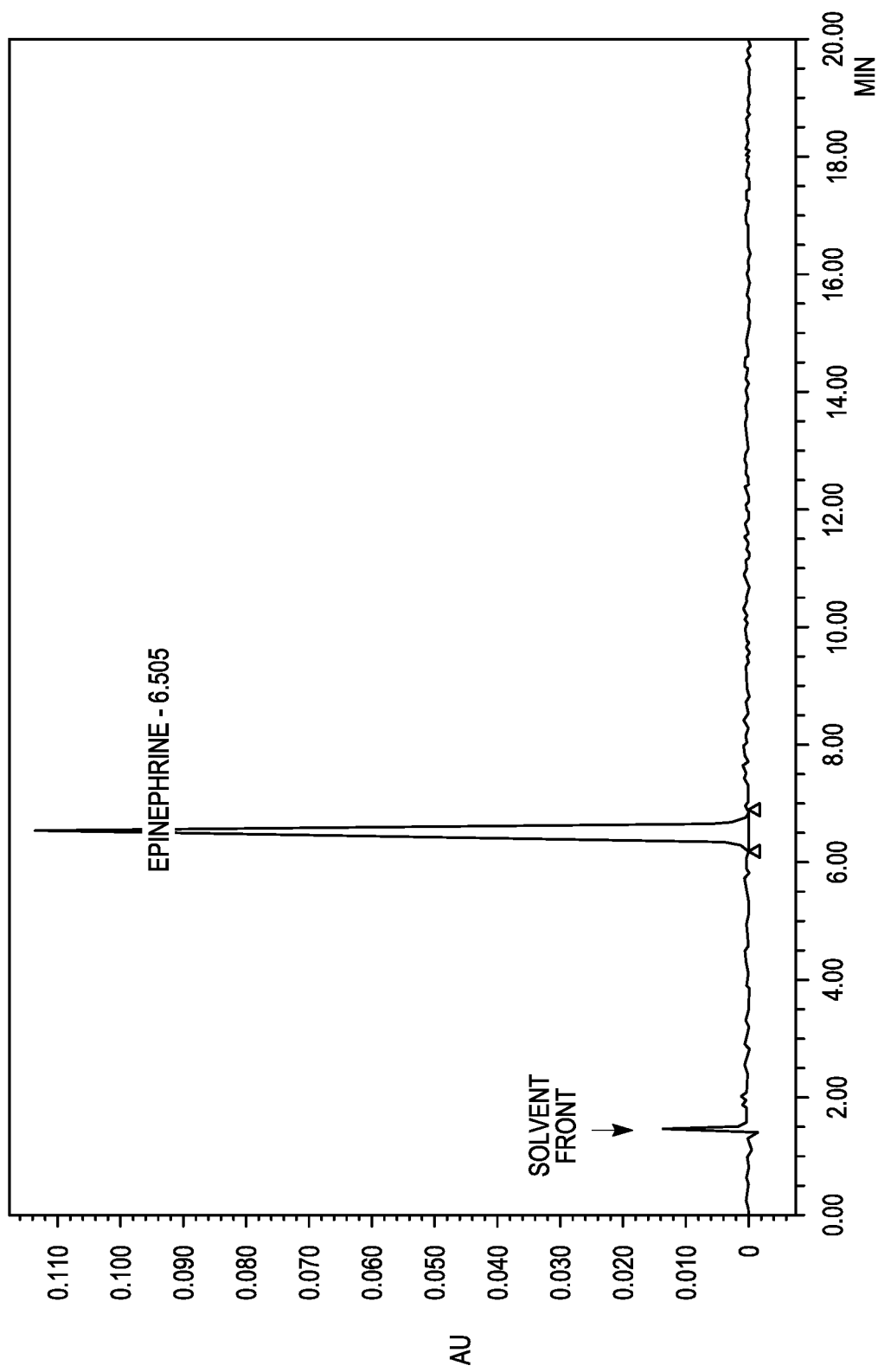
FIG. 6 illustrates the HPLC chromatogram of epinephrine stability in SBEßCD formulation after 6 months at 40° C.
Figure 7:
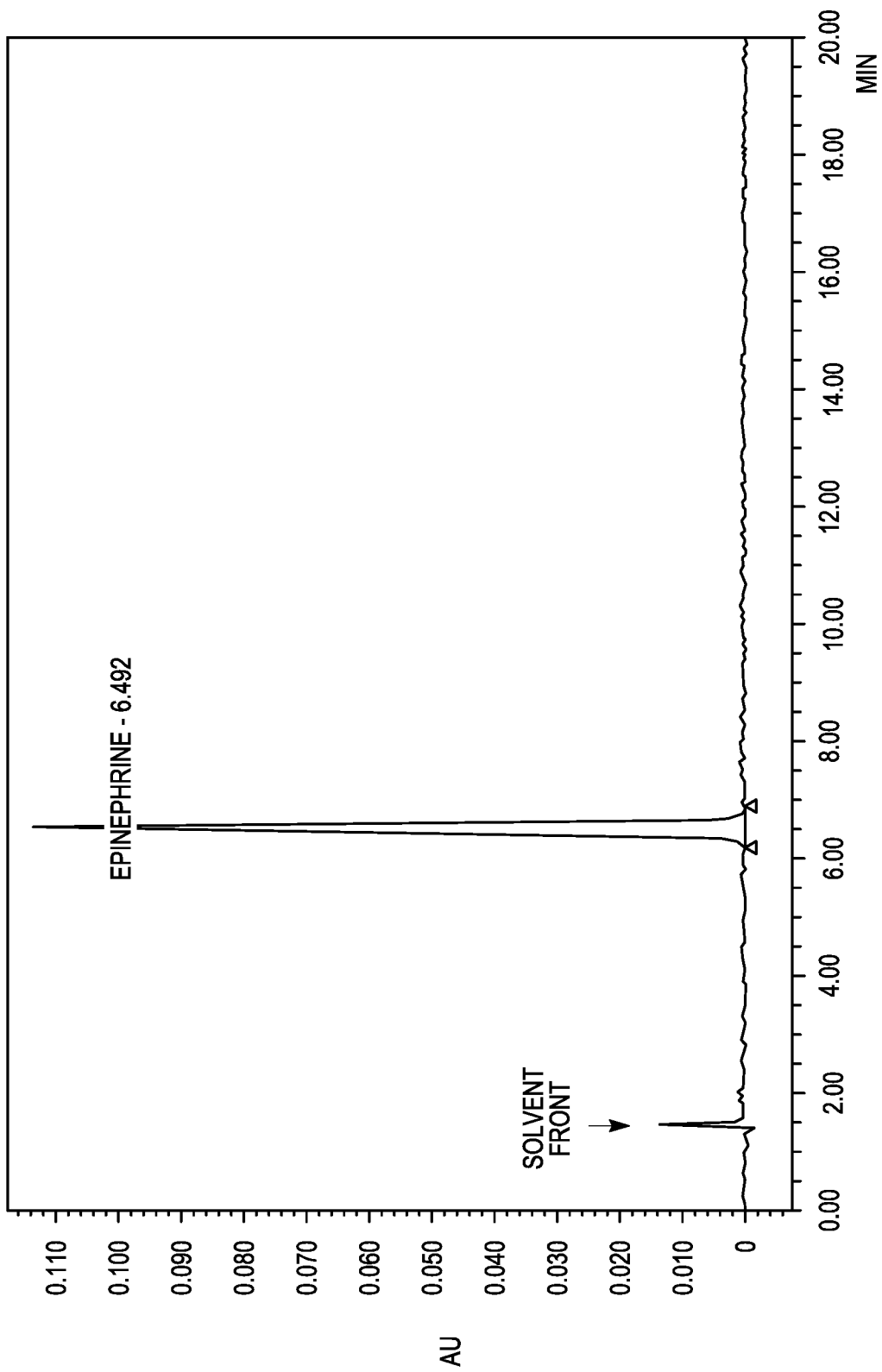
FIG. 7 illustrates the HPLC chromatogram of epinephrine stability in HPßCD formulation after 6 months at 40° C.

Examples of HPLC chromatograms demonstrating novel physicochemical stability improvements in SBEßCD and HPßCD formulations with insignificant degradant levels in the present invention are illustrated in FIGS. 3 and 4, respectively.

TABLE 5

Stabilities of epinephrine complex formulations containing about 0.01 wt. % antioxidant (cysteine) (1:10 weight ratio of cysteine-to-drug) and a commercial formulation after 1 month storage at 50° C.

| Example | CD | Potency (%) | ESA (%) | pH | Appearance | O.D. |
|---|---|---|---|---|---|---|
| 9 | SBEβCD | 100.1 | ND | 2.5 | Clear, colorless & no particulates | 0.0059 |
| 10 | HPβCD | 99.5 | ND | 2.5 | Clear, colorless & no particulates | 0.0060 |
| 33 (Commercial Formulation) | None | 74.0 | >37 | 3.4 | Slightly brownish-tan | N/A |
| 0.0005N Iodine | None | NA | NA | NA | Slightly brownish | 0.1354 |

ND = Not detected;
NA = Not Applicable;
O.D. = Optical density (Absorbance at λmax = 485 nm)

The physicochemical improvement of epinephrine was also discovered in a non-complex formulation containing low levels of cysteine (0.01 and 0.03 wt. % or 1:10 and 3:10 weight ratio of cysteine-to-drug in Example 11 and 12, respectively) to be ~99% drug potency compared to ~90-97% at higher levels (0.05, 0.07 and 0.1 wt. % or 5:10, 7:10 and 1:1 weight ratio of cysteine-to-drug in Example 13, 14 and 15, respectively) after 1 month storage at 50° C. as shown in TABLE 6.

TABLE 6

Stabilities of non-complex epinephrine formulations at different antioxidant levels of cysteine after 1 month storage at 50° C.

| Example | Cysteine:Drug | Potency (%) | Degradant (% peak area) | pH | Appearance | O.D. |
|---|---|---|---|---|---|---|
| 11 | 1:10 | 98.7 | ND | 2.5 | Clear, colorless & no particulates | 0.0028 |
| 12 | 3:10 | 99.2 | ND | 2.5 | Clear, colorless & no particulates | 0.0019 |

TABLE 6-continued

Stabilities of non-complex epinephrine formulations at different antioxidant levels of cysteine after 1 month storage at 50° C.

| Example | Cysteine:Drug | Potency (%) | Degradant (% peak area) | pH | Appearance | O.D. |
|---|---|---|---|---|---|---|
| 13 | 5:10 | 97.4 | 2.6 | 2.5 | Clear, colorless & no particulates | 0.0025 |
| 14 | 7:10 | 95.0 | 5.0 | 2.5 | Clear, colorless & no particulates | 0.0029 |
| 15 | 1:1 | 89.8 | 11.2 | 2.5 | Clear, colorless & no particulates | 0.0038 |
| 0.0005N Iodine | N/A | NA | NA | NA | Slightly brownish | 0.1354 |

ND = Not detected;
NA = Not Applicable;
O.D. = Optical density (Absorbance at λmax = 485 nm)

The physicochemical improvement of epinephrine was also discovered in a non-complex formulation containing low levels of thioglycerol (0.0, 0.03, 0.05 and 0.07 wt. % or 1:10, 3; 10, 5:10 and 7:10 weight ratio of thioglycerol in Examples 16, 17, 18, 19 and 20, respectively) to be ~99% drug potency compared to ~97% at a higher level (0.1 wt. % or 1:1 weight ratio of thioglycerol in Example 20) after 1 month storage at 50° C. as shown in TABLE 7.

TABLE 7

Stabilities of non-complex epinephrine formulations at different antioxidant levels of thioglycerol after 1 month storage at 50° C.

| Example | Thioglycerol:Drug | Potency (%) | Degradant (% peak area) | pH | Appearance | O.D. |
|---|---|---|---|---|---|---|
| 16 | 1:10 | 99.2 | ND | 2.5 | Clear, colorless & no particulates | 0.0018 |
| 17 | 3:10 | 99.1 | ND | 2.5 | Clear, colorless & no particulates | 0.0023 |
| 18 | 5:10 | 98.9 | ND | 2.5 | Clear, colorless & no particulates | 0.0022 |
| 19 | 7:10 | 99.2 | ND | 2.5 | Clear, colorless & no particulates | 0.0019 |
| 20 | 1:1 | 97.3 | 2.7 | 2.5 | Clear, colorless & no particulates | 0.0025 |
| 0.0005N Iodine | N/A | NA | NA | NA | Slightly brownish | 0.1354 |

ND = Not detected;
NA = Not Applicable;
O.D. = Optical density (Absorbance at λmax = 485 nm)

The physicochemical improvement of epinephrine was also discovered in a non-complex formulation containing low levels of acetylcysteine (0.0, 0.03, 0.05 and 0.07 wt. % or 1:10, 3; 10, 5:10 and 7:10 weight ratio of acetylcysteine in Examples 21, 22, 23 and 24, respectively) to be ~99% drug potency compared to ~97% at a higher level (0.1 wt. % or 1:1 weight ratio of acetylcysteine in Example 25) after 1 month storage at 50° C. as shown in TABLE 8.

TABLE 8

Stabilities of non-complex epinephrine formulations at different antioxidant levels of acetylcysteine after 1 month storage at 50° C.

| Example | Acetylcysteine:Drug | Potency (%) | Degradant (% peak area) | pH | Appearance | O.D. |
|---|---|---|---|---|---|---|
| 21 | 1:10 | 99.9 | ND | 2.5 | Clear, colorless & no particulates | 0.0022 |
| 22 | 3:10 | 97.6 | ND | 2.5 | Clear, colorless & no particulates | 0.0019 |
| 23 | 5:10 | 100.4 | ND | 2.5 | Clear, colorless & no particulates | 0.0028 |
| 24 | 7:10 | 98.8 | ND | 2.5 | Clear, colorless & no particulates | 0.0015 |

TABLE 8-continued

Stabilities of non-complex epinephrine formulations at different antioxidant levels of acetylcysteine after 1 month storage at 50° C.

| Example | Acetylcysteine:Drug | Potency (%) | Degradant (% peak area) | pH | Appearance | O.D. |
|---|---|---|---|---|---|---|
| 25 | 1:1 | 97.0 | 3.0 | 2.5 | Clear, colorless & no particulates | 0.0023 |
| 0.0005N Iodine | N/A | NA | NA | NA | Slightly brownish | 0.1354 |

ND = Not detected;
NA = Not Applicable;
O.D. = Optical density (Absorbance at λmax = 485 nm)

The physicochemical improvement of epinephrine was also discovered in a non-complex formulation containing low levels of mixed antioxidants at 0.01 wt. % or 1:10 weight ratio of each antioxidant to drug. The formulations of mixed antioxidants of cysteine/acetylcysteine, cystenine/thioglycerol and thioglycerol/acetylcysteine are described Examples 26, 27 and 28, respectively. All combinations of mixed antioxidants demonstrated the drug potency to be ~99-100% after 1 month storage at 50° C. as shown in TABLE 9.

TABLE 9

Stabilities of non-complex epinephrine formulations using mixed antioxidants at 1:10 ratio of antioxidant to drug or 0.01 wt. % after 1 month storage at 50° C.

| Example | Antioxidants | Potency (%) | Degradant (% peak area) | pH | Appearance | O.D. |
|---|---|---|---|---|---|---|
| 26 | Cysteine/Acetylcysteine | 99.5 | ND | 2.5 | Clear, colorless & no particulates | 0.0022 |
| 27 | Cysteine/Thioglycerol | 99.5 | ND | 2.5 | Clear, colorless & no particulates | 0.0019 |
| 28 | Thioglycerol/Acetylcysteine | 98.6 | ND | 2.5 | Clear, colorless & no particulates | 0.0028 |
| 0.0005N Iodine | N/A | NA | NA | NA | Slightly brownish | 0.1354 |

ND = Not detected;
NA = Not Applicable;
O.D. = Optical density (Absorbance at λmax = 485 nm)

The pediatric formulations of epinephrine injection (1:2000) for anaphylaxis treatment were also explored to enhance their physicochemical stabilities and extend the product shelf lives. The non-complex formulations were investigated using a single antioxidant in Example 29 or mixed antioxidants in Examples 30-32. The physicochemical stability improvements were discover in all formulations with the drug potency greater than 99% as shown in Table 10.

TABLE 10

Stabilities of non-complex pediatric epinephrine formulations (1:2000) using single or mixed antioxidants at 1:10 ratio of antioxidant to drug or 0.01 wt. % after 1 month storage at 50° C.

| Example | Antioxidant(s) | Potency (%) | Degradant (% peak area) | pH | Appearance | O.D. |
|---|---|---|---|---|---|---|
| 29 | Cysteine | 100.0 | ND | 2.5 | Clear, colorless & no particulates | 0.0020 |
| 30 | Cysteine/Acetylcysteine | 99.2 | ND | 2.5 | Clear, colorless & no particulates | 0.0017 |
| 31 | Cysteine/Thioglycerol | 99.7 | ND | 2.5 | Clear, colorless & no particulates | 0.0025 |
| 32 | Thioglycerol/Acetylcysteine | 99.7 | ND | 2.5 | Clear, colorless & no particulates | 0.0013 |
| 0.0005N Iodine | N/A | NA | NA | NA | Slightly brownish | 0.1354 |

ND = Not detected;
NA = Not Applicable;
O.D. = Optical density (Absorbance at λmax = 485 nm)

The physicochemical stabilities of two complex formulations (Examples 9 and 10) were also evaluated and compared with a commercial product at a longer accelerated stability condition at 40° C./75% RH for six months under a guidance from ICH (The International Council for Harmonization of Technical Requirements for Pharmaceuticals for Human Use).

After six months under an ICH storage condition at 40° C./75% RH, epinephrine in the commercial formulation was rapidly degraded to be ~79% compared to >95% of certain exemplified formulations in the present invention. The degradation products in the commercial formulation mainly epinephrine sulfonic acid (ESA) was found ~32% compared to "not detected" levels in both formulations of the present invention. The testing results are summarized and presented in TABLE 11.

TABLE 11

Physicochemical stabilities of epinephrine complex formulations containing 0.01 wt. % antioxidant (cysteine) (1:10 weight ratio of cysteine-to-drug) and a typical commercial "sulfite" formulation after 6 month storage at 40° C./75% RH

| Example | CD | Potency (%) | ESA (%) | pH | Appearance |
|---|---|---|---|---|---|
| 9 | SBEβCD | >95 | ND | 2.6 | Clear, colorless & no particulates |
| 10 | HPβCD | >95 | ND | 2.6 | Clear, colorless & no particulates |
| 33 (Commercial Formulation) | None | 79.1 | 31.8 | 3.4 | Clear, colorless & no particulates |

ND = Not detected

After twelve (12) months under an ICH storage condition at 25° C./60% RH, epinephrine in all commercial formulations including EpiPen, Adrenaclick and Auvi-Q were similarly degraded to be ~91-93% from their initial values at 110-112% overages compared to ~100% from that at 100% target of certain exemplified formulations in the present invention. The degradation products in the commercial formulations mainly epinephrine sulfonic acid (ESA) was found ~9-11% compared to "not detected" levels in both formulations of the present invention. The testing results are summarized and presented in TABLE 8.

TABLE 8

Physicochemical stabilities of epinephrine complex formulations containing about 0.01 wt. % antioxidant (cysteine) (1:10 weight ratio of cysteine-to-drug) and the other commercial products after 12 month storage at 25° C./60% RH

| Example | CD | Potency (%) | ESA (%) | pH | Appearance |
|---|---|---|---|---|---|
| 9 | SBEβCD | ~100 | ND | 2.5 | Clear, colorless & no particulates |
| 10 | HPβCD | ~100 | ND | 2.5 | Clear, colorless & no particulates |
| EpiPen Adrenaclick Auvi-Q | None | ~91-93 | ~9-11 | 2.5-4.5 | Clear, colorless & no particulates |

ND = Not detected

Figure 8:
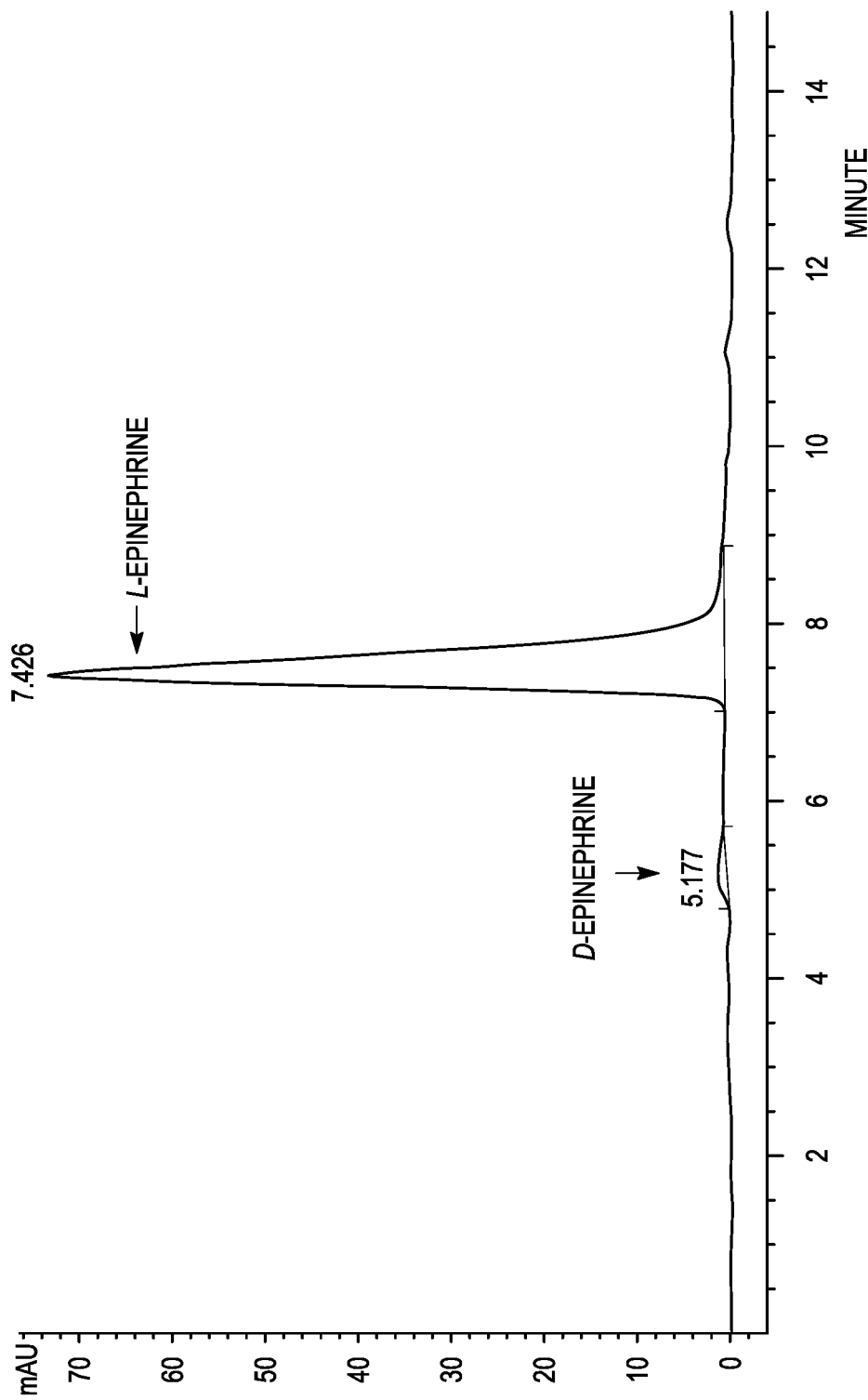
FIG. 8 illustrates the HPLC chromatogram of epinephrine chirality in SBEßCD formulation after 3.5 months at 40° C.
Figure 9:
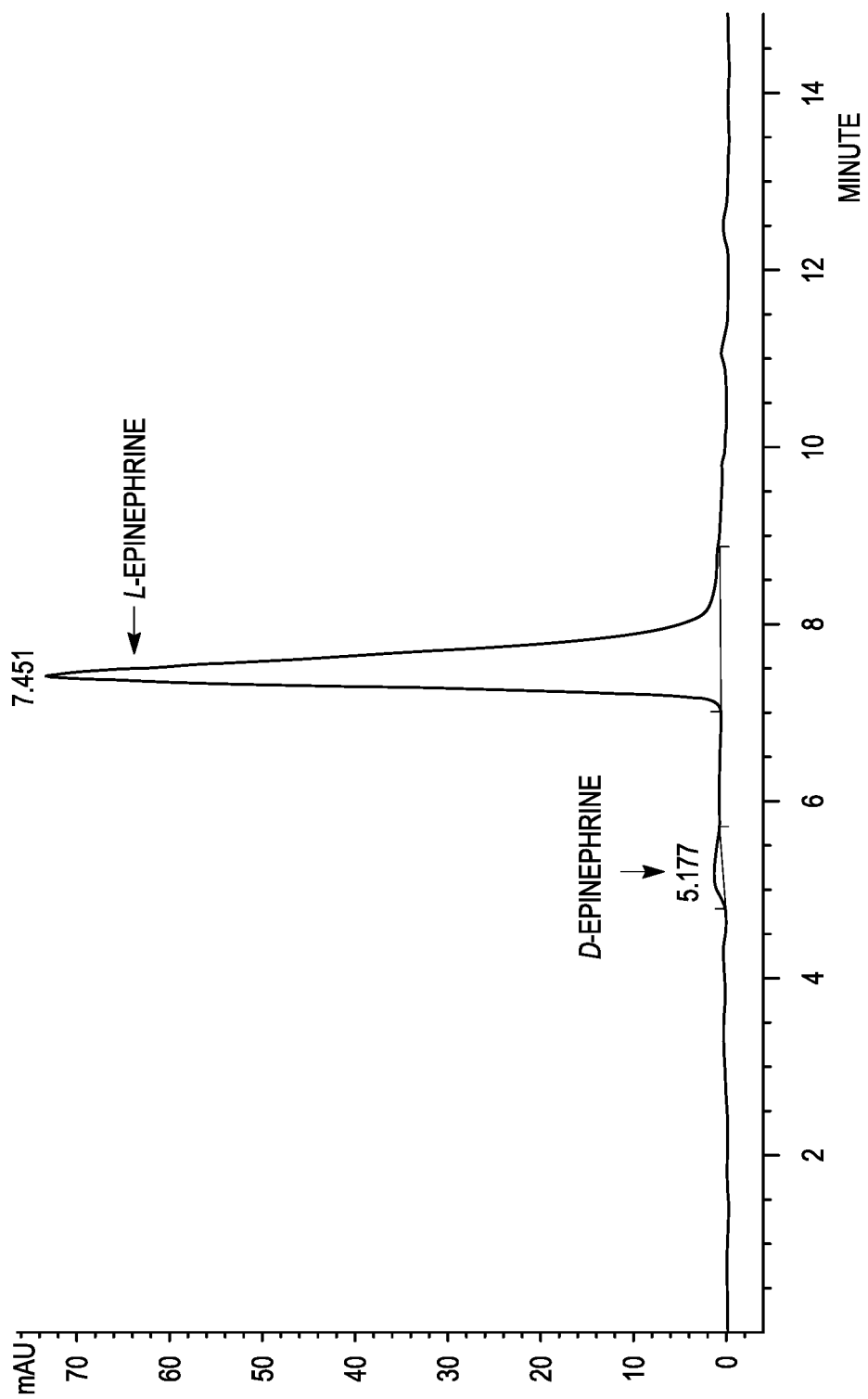
FIG. 9 illustrates the HPLC chromatogram of epinephrine chirality in HPßCD formulation after 3.5 months at 40° C.

In addition, after 3.5 months under ICH storage condition at 40° C./75% RH, the chirality of epinephrine racemization was also found <3% d-epinephrine in both complex formulations (Examples 9 & 10) as shown in TABLE 9. Examples of HPLC chromatograms demonstrating drug racemization in both SBEßCD and HPßCD formulations are shown in FIGS. 8 and 9, respectively.

TABLE 9

Chirality of epinephrine complex formulations at pH 2.5 after 3.5 month storage at 40° C./75% RH

| | | d-Epinephrine (%) | | |
|---|---|---|---|---|
| Example | CD | Initial | 3.5 Months | Appearance |
| 9 | SBEβCD | 1.4 | 2.9 | Clear, colorless & no particulates |
| 10 | HPβCD | 1.4 | 1.7 | Clear, colorless & no particulates |

Example 34

Epinephrine formulations as described herein are indicated in the treatment (e.g., emergency treatment) of allergic reactions (e.g., Type I) including, for example, anaphylaxis to stinging insects (e.g., order Hymenoptera, which include bees, wasps, hornets, yellow jackets and fire ants) and biting insects (e.g., triatoma, mosquitoes), allergen immunotherapy, foods, drugs, diagnostic testing substances (e.g., radiocontrast media) and other allergens, as well as idiopathic anaphylaxis or exercise-induced anaphylaxis. Epinephrine formulations in the present invention are intended for immediate administration in patients who are determined to be at increased risk for anaphylaxis, including individuals with a history of anaphylactic reactions.

Anaphylactic reactions may occur within minutes after exposure and consist of flushing, apprehension, syncope, tachycardia, thready or unobtainable pulse associated with a fall in blood pressure, convulsions, vomiting, diarrhea and abdominal cramps, involuntary voiding, wheezing, dyspnea due to laryngeal spasm, pruritus, rashes, urticaria or angioedema. Epinephrine formulations in the present invention are intended for immediate administration as emergency supportive therapy only and are not a substitute for immediate medical care.

Selection of the appropriate dosage strength of the epinephrine formulations (e.g., a formulation of any one of Examples 9-31) is determined according to patient body weight. Patients greater than or equal to 30 kg (approximately 66 pounds or more) are required 0.3 mg dose or 0.3 mL epinephrine formulation (1:1000). Patients of 15 to 30 kg (33 pounds to 66 pounds) are required 0.15 mg dose or 0.15 mL epinephrine formulation (1:1000) or alternatively 0.3 mL epinephrine formulation (1:2000). The epinephrine formulation is intramuscularly or subcutaneously injected into the anterolateral aspect of the thigh, through clothing if necessary.

The prescriber should carefully assess each patient to determine the most appropriate dose of epinephrine, recognizing the life-threatening nature of the reactions for which this drug is indicated. With severe persistent anaphylaxis, repeat injections may be necessary. More than two sequential doses of epinephrine should only be administered under direct medical supervision.

Epinephrine formulation should only be injected into the anterolateral aspect of the thigh. Do not inject intravenously. Rapidly acting vasodilators can counteract the marked pressor effects of epinephrine if there is such inadvertent administration. Do not inject into digits, hands or feet. Since epinephrine is a strong vasoconstrictor when injected into the digits, hands, or feet, treatment should be directed at vasodilatation if there is such an accidental injection to these areas. Do not inject into buttock. If there is an accidental injection into these areas, advise the patient to inform the healthcare provider of the accidental injection when he/she goes to the nearest emergency room for further treatment of anaphylaxis.

Epinephrine should be administered with caution to patients who have heart disease, including patients with cardiac arrhythmias, coronary artery or organic heart disease, or hypertension. In such patients, or in patients who are on drugs that may sensitize the heart to arrhythmias, epinephrine may precipitate or aggravate angina pectoris as well as produce ventricular arrhythmias. Epinephrine should be administered with caution to patients with hyperthyroidism, diabetes, elderly individuals, and pregnant women. Patients with Parkinson's disease may notice a temporary worsening of symptoms.

Unlike all commercial products currently available on the market, certain epinephrine formulations in the present invention are a "sulfite free" formulation and safe for the sulfite-sensitive patient.

What is claimed is:

1. A pharmaceutical composition comprising:
   l-epinephrine;
   free of an epinephrine degradation product, the epinephrine degradation product being epinephrine sulfonic acid (ESA);
   one or more antioxidant, the antioxidant being present in the composition in an amount of about 0.005 wt. % to about 0.03 wt. %, wherein the one or more antioxidant comprises cysteine, thioglycerol, or any combination thereof; and
   an aqueous medium;
   wherein the pharmaceutical composition has a pH of about 2.5 to about 3.5 and a weight ratio of the antioxidant to l-epinephrine is about 1:10 to about 7:10.

2. The pharmaceutical composition of claim 1, wherein the one or more antioxidant is cysteine.

3. The pharmaceutical composition of claim 1, wherein (i) after six months of storage at 40±2° C. and 75±5% relative humidity (RH), the composition comprises at least 90 wt. % of the l-epinephrine in the composition prior to storage; (ii) after 12 months of storage at 25±2° C. and 60±5% relative humidity (RH) the composition comprises at least 90 wt. % of the l-epinephrine in the composition prior to storage; and (iii) after 12 months of storage at 25±2° C. and 60±5% relative humidity (RH) the composition is substantially colorless.

4. The pharmaceutical composition of claim 1, wherein after at least 1 year of storage at 25° C./60% RH, less than 10% of the l-epinephrine is d-epinephrine.

5. The pharmaceutical composition of claim 1, wherein the l-epinephrine is present in the composition in an amount of about 0.01 wt. % to about 1 wt. % on a free base basis.

6. The pharmaceutical composition of claim 1, wherein the l-epinephrine is present in the composition in an amount of about 0.05 wt. % to about 0.15 wt. % on a free base basis.

7. The pharmaceutical composition of claim 1, further comprising a complexing agent, wherein the complexing agent is one or more cyclodextrin.

8. The pharmaceutical composition of claim 7, wherein the cyclodextrin is present in the composition in a molar ratio of cyclodextrin-to-l-epinephrine of about 1:10 to about 10:1.

9. The pharmaceutical composition of claim 8, wherein the cyclodextrin is present in the composition in a molar ratio of cyclodextrin-to-l-epinephrine of about 1:3 to about 2:1.

10. The pharmaceutical composition of claim 1, further comprising one or more pH buffering agent, the combined weight of pH buffering agent(s) constituting about 0.01 wt. % or less of the composition.

11. The pharmaceutical composition of claim 1, further comprising an edetate, the edetate being present in the composition in an amount of about 0.01 wt. % or less.

12. The pharmaceutical composition of claim 1, wherein a tonicity modifier is present in the composition in an amount suitable to provide a solution osmolality in the range of about 200 mOsm/kg to about 400 mOsm/kg.

* * * * *